US010771676B2

(12) United States Patent
Yoshino

(10) Patent No.: US 10,771,676 B2
(45) Date of Patent: Sep. 8, 2020

(54) FOCUS CONTROL DEVICE, ENDOSCOPE APPARATUS, AND METHOD FOR OPERATING FOCUS CONTROL DEVICE

(71) Applicant: OLYMPUS CORPORATION, Tokyo (JP)

(72) Inventor: Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 121 days.

(21) Appl. No.: 16/030,165

(22) Filed: Jul. 9, 2018

(65) Prior Publication Data
US 2018/0316870 A1 Nov. 1, 2018

Related U.S. Application Data

(63) Continuation of application No. PCT/JP2016/051139, filed on Jan. 15, 2016.

(51) Int. Cl.
H04N 5/232 (2006.01)
A61B 1/04 (2006.01)
(Continued)

(52) U.S. Cl.
CPC ... *H04N 5/232123* (2018.08); *A61B 1/00009* (2013.01); *A61B 1/00188* (2013.01);
(Continued)

(58) Field of Classification Search
CPC ....... H04N 5/232123; H04N 5/232127; H04N 5/23254; H04N 5/23287;
(Continued)

(56) References Cited

U.S. PATENT DOCUMENTS 6,222,587 B1  4/2001 Ito et al.
2004/0223073 A1  11/2004 Kanai
(Continued)

FOREIGN PATENT DOCUMENTS

JP H09061705 A 3/1997
JP H09200508 A 7/1997
(Continued)

OTHER PUBLICATIONS

Japanese Office Action dated Oct. 29, 2019 in Japanese Patent Application No. 2017-561487.
(Continued)

*Primary Examiner* — Twyler L Haskins
*Assistant Examiner* — Fayez Bhuiyan
(74) *Attorney, Agent, or Firm* — Scully, Scott, Murphy & Presser, P.C.

(57) ABSTRACT

A focus control device includes a region setting section 2010 that sets a plurality of regions, each including a plurality of pixels, to an image acquired by an imaging section 200, an AF evaluation value calculation section 2020 that calculates an AF evaluation value of each of the plurality of regions, an invalid region setting section (invalid block setting section 2050) that sets an invalid region (low contrast determination invalid block) in the plurality of regions, a low contrast state determination section 2075 that determines whether or not the target subject is in a low contrast state based on the AF evaluation value of a region, in the plurality of regions, other than the invalid region, and a focus control section 2000 that controls an in-focus object plane position based on the AF evaluation value. The focus control section 2000 is configured to implement the focus control varying depending on a determination result obtained by the low contrast state determination section 2075.

15 Claims, 22 Drawing Sheets

(51) Int. Cl.
  *A61B 1/00* (2006.01)
  *H04N 5/225* (2006.01)
(52) U.S. Cl.
  CPC ......... *A61B 1/042* (2013.01); *H04N 5/23254* (2013.01); *H04N 5/23287* (2013.01); *H04N 5/232127* (2018.08); *H04N 2005/2255* (2013.01)
(58) Field of Classification Search
  CPC ........ H04N 2005/2255; A61B 1/00009; A61B 1/00188; A61B 1/042
  See application file for complete search history.

(56) References Cited

U.S. PATENT DOCUMENTS

| | | |
|---|---|---|
| 2011/0032411 A1 | 2/2011 | Hirai |
| 2012/0033105 A1* | 2/2012 | Yoshino ............. A61B 1/00009 348/239 |
| 2013/0188029 A1 | 7/2013 | Takahashi |
| 2014/0039257 A1 | 2/2014 | Higuchi et al. |
| 2014/0210974 A1 | 7/2014 | Yoshino |
| 2015/0334289 A1 | 11/2015 | Yoshino |
| 2016/0156835 A1 | 6/2016 | Ogasawara et al. |
| 2016/0234427 A1 | 8/2016 | Yoshino |
| 2018/0316871 A1 | 11/2018 | Yoshino |

FOREIGN PATENT DOCUMENTS

| | | |
|---|---|---|
| JP | 2004264827 A | 9/2004 |
| JP | 2006245792 A | 9/2006 |
| JP | 2011022404 A | 2/2011 |
| JP | 2011039213 A | 2/2011 |
| JP | 2011139760 A | 7/2011 |
| JP | 2012-103394 A | 5/2012 |
| JP | 2012103394 A | 5/2012 |
| JP | 2013088766 A | 5/2013 |
| JP | 2013150658 A | 8/2013 |
| JP | 2013183836 A | 9/2013 |
| JP | 2014030516 A | 2/2014 |
| JP | 2014145808 A | 8/2014 |
| JP | 2015123293 A | 7/2015 |
| JP | 5829360 B2 | 12/2015 |
| WO | 2015050008 A1 | 4/2015 |
| WO | 2015098218 A1 | 7/2015 |

OTHER PUBLICATIONS

International Search Report dated Apr. 12, 2016 issued in PCT/JP2016/051139.
International Search Report dated Apr. 19, 2016 issued in PCT/JP2016/051138.

* cited by examiner

FOCUS CONTROL DEVICE, ENDOSCOPE APPARATUS, AND METHOD FOR OPERATING FOCUS CONTROL DEVICE

CROSS REFERENCE TO RELATED APPLICATION

This application is a continuation of International Patent Application No. PCT/JP2016/051139, having an international filing date of Jan. 15, 2016, which designated the United States, the entirety of which is incorporated herein by reference.

BACKGROUND

A depth of field as deep as possible is required for an endoscope system so that a user can easily perform diagnosis and treatment. In recent years, the depth of field of an endoscope system has become shallow along with the use of an image sensor having a large number of pixels. In view of this, an endoscope system that performs an autofocus (AF) process has been proposed.

In an apparatus, such as an endoscope system, involving monitoring a movie, AF is preferably performed based on wobbling. However, the AF based on the wobbling might continue to fail to bring a subject into focus due to a failure to determine an in-focus direction in a largely blurred state, as a result of an erroneous operation of the AF or the like. In the largely blurred state, a wobbling operation can only provide an extremely small change in an AF evaluation value. In view of this, in a video camera and the like, a subject is determined to be in a largely blurred state (a low contrast state in a broad sense) when a change in the AF evaluation value is extremely small. Then, a control is performed to search for an in-focus position by performing scanning using a focus lens.

For example, JP-A-2011-22404 discloses a method of acquiring a plurality of images with different aperture stops, and determining that a subject is in a largely blurred state when the change in the AF evaluation value is small.

JP-A-2006-245792 discloses an AF control method proposed for a case where a captured image includes a subject (obstacle) other than a target subject. Specifically, in a case where there is an obstacle between the target subject and an imaging device, the target subject is brought into focus with the obstacle designated by a user.

SUMMARY

According to one aspect of the invention, there is provided a focus control device comprising a processor including hardware, the processor being configured to implement:

a region setting process of setting a plurality of regions, each including a plurality of pixels, to an image acquired by an imaging section;

an AutoFocus (AF) evaluation value calculation process of calculating an AF evaluation value of each of the plurality of regions set;

an invalid region setting process of setting a region, in the plurality of regions, determined to include a subject other than a target subject to be an invalid region;

a low contrast state determination process of determining whether or not the target subject is in a low contrast state based on the AF evaluation value of a region, in the plurality of regions, other than the invalid region; and focus control of controlling an in-focus object plane position based on the AF evaluation value, the processor being configured to implement the focus control varying depending on a determination result obtained by the low contrast state determination process.

According to another aspect of the invention, there is provided an endoscope apparatus comprising the focus control device as defined above.

According to another aspect of the invention, there is provided a method for operating a focus control device, the method comprising:

setting a plurality of regions, each including a plurality of pixels, to an image acquired by an imaging section;

calculating an AutoFocus (AF) evaluation value of each of the plurality of regions set;

setting a region, in the plurality of regions, determined to include a subject other than a target subject to be an invalid region;

determining whether or not the target subject is in a low contrast state based on the AF evaluation value of a region, in the plurality of regions, other than the invalid region; and controlling an in-focus object plane position based on the AF evaluation value and a result of determining whether or not the target subject is in a low contrast state.

DESCRIPTION OF EXEMPLARY EMBODIMENTS

Figure 1:
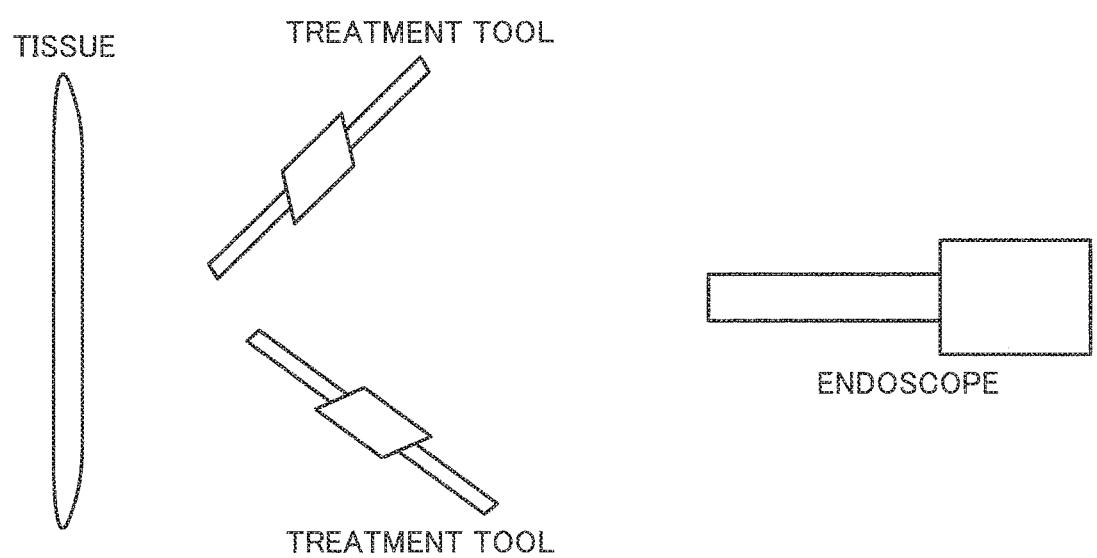
FIG. 1 illustrates an example of positional relationship between an endoscope apparatus (imaging section) and subjects (tissue, treatment tool).

According to one embodiment of the invention, there is provided a focus control device comprising a processor including hardware, the processor being configured to implement:

a region setting process of setting a plurality of regions, each including a plurality of pixels, to an image acquired by an imaging section;

an AutoFocus (AF) evaluation value calculation process of calculating an AF evaluation value of each of the plurality of regions set;

an invalid region setting process of setting a region, in the plurality of regions, determined to include a subject other than a target subject to be an invalid region;

a low contrast state determination process of determining whether or not the target subject is in a low contrast state based on the AF evaluation value of a region, in the plurality of regions, other than the invalid region; and focus control of controlling an in-focus object plane position based on the AF evaluation value, the processor being configured to implement the focus control varying depending on a determination result obtained by the low contrast state determination process.

According to another embodiment of the invention, there is provided an endoscope apparatus comprising the focus control device as defined above.

According to another embodiment of the invention, there is provided a method for operating a focus control device, the method comprising:

setting a plurality of regions, each including a plurality of pixels, to an image acquired by an imaging section;

calculating an AutoFocus (AF) evaluation value of each of the plurality of regions set;

setting a region, in the plurality of regions, determined to include a subject other than a target subject to be an invalid region;

determining whether or not the target subject is in a low contrast state based on the AF evaluation value of a region, in the plurality of regions, other than the invalid region; and controlling an in-focus object plane position based on the AF evaluation value and a result of determining whether or not the target subject is in a low contrast state.

Exemplary embodiments of the invention are described below. Note that the following exemplary embodiments do not in any way limit the scope of the invention laid out in the claims. Note also that not all of the elements described below in connection with the exemplary embodiments should be taken as essential elements of the invention.

1. METHOD ACCORDING TO PRESENT EMBODIMENT

1.1 Overview of Low Contrast State Determination

First of all, a method according to the present embodiment is described. In an apparatus, such as an endoscope apparatus (endoscope system) involving monitoring a movie, auto focusing (AF) is preferably performed based on wobbling. Alternatively, a wide range may be scanned with a focus lens. For example, a peak AF evaluation value may be obtained with the focus lens moving between a near end point and a far end point. Unfortunately, this is not preferable in terms of monitoring, because the level of focusing (level of blurring) of an image constantly largely changes during the scanning.

The wobbling only involves a small movement width (a wobbling amount described later with reference to FIG. 8A) of the focus lens, for determining an in-focus direction. Thus, in a largely blurred state, with the image largely blurred, the in-focus direction cannot be appropriately determined with the wobbling only providing an extremely small amount of change in the AF evaluation value. Specifically, a large difference between the position of a subject and an in-focus object plane position results in the largely blurred state.

In the largely blurred state, the in-focus direction cannot be determined and thus the AF might continue only to result in a failure to bring the subject into focus. In view of the above, the largely blurred state needs to be appropriately detected, and a reset operation is required to be performed to resolve the largely blurred state.

Even when the AF control appropriately works without any error, the wobbling results in an extremely small amount (rate) of change in the AF evaluation value if the subject has a low contrast, that is, if the subject has an extremely small amount of unevenness or an extremely small change in tone for example. As a result, the in-focus direction determination ends in a failure. The low contrast is a factor on the subject side, and thus performing the reset operation for the sake of focusing through the wobbling could hardly be expected to succeed in the low contrast state. Still, it is important to detect that the subject has a low contrast since the continued AF based on the wobbling is ineffective in such a situation.

As described above, there has been a demand for detecting the largely blurred state or detecting a state where an image of a low contrast subject is being captured (hereinafter, referred to as a low contrast state). JP-A-2011-22404 discloses one method of detecting the largely blurred state. However, a conventional method disclosed in JP-A-2011-22404 or the like remains silent on a case where a captured image includes a target subject and other subjects (obstacles).

For example, an endoscopic procedure involves ablating a lesioned part, suturing, and the like. Thus, a treatment tool might be disposed between a tissue that is a focusing target and an endoscope apparatus serving as an imaging device as illustrated in FIG. 1. This treatment tool is a tool used for a treatment for a tissue. Specific examples of the treatment tool include an energy device (such as an electrocauter), forceps, and the like. Generally, the treatment tool has a higher contrast than the subject. Thus, a high AF evaluation value of the treatment tool might render the low contrast state of the subject undetectable, resulting in the wobbling continuing in vain. For example, a failure to detect the largely blurred state with the position of the target subject (tissue) being largely different from an in-focus object plane position or to detect the low contrast state of the target subject, leads to the AF based on the wobbling continuing in vain, resulting in a failure to bring the tissue serving as the target subject of the user into focus.

Figure 2:
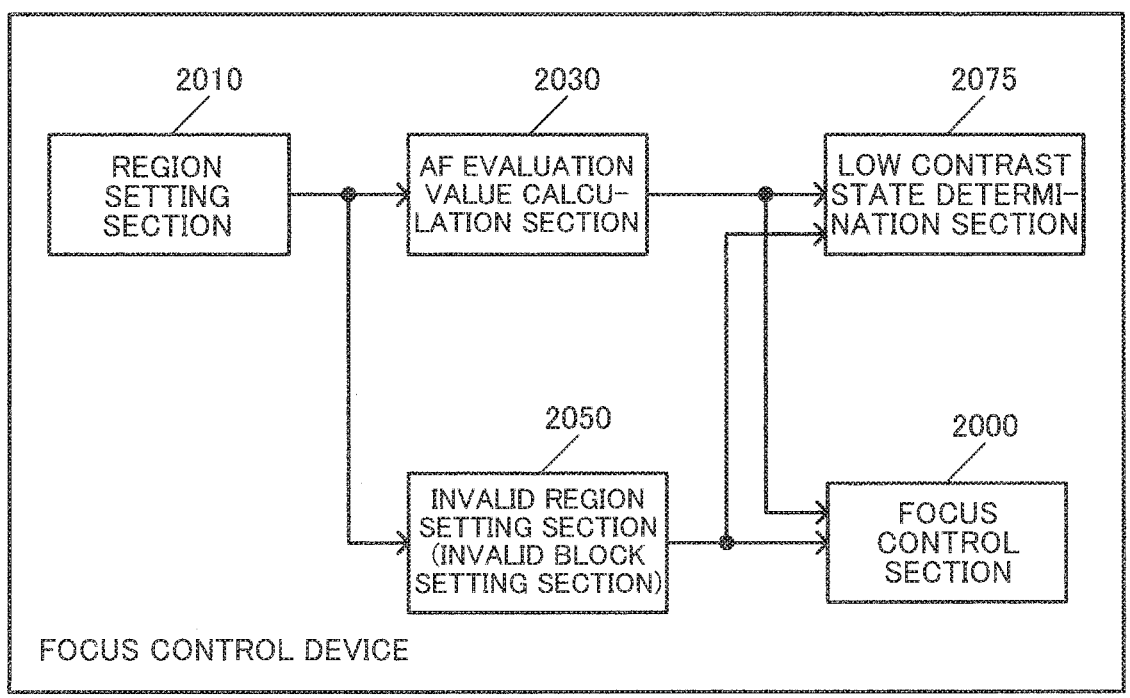
FIG. 2 illustrates a basic configuration example of a focus control device.

In view of this, the present applicant proposes the following focus control device. As illustrated in FIG. 2, the focus control device according to the present embodiment includes a region setting section 2010, an AF evaluation value calculation section (block AF evaluation value calculation section) 2030, an invalid region setting section (invalid block setting section) 2050, a low contrast state determination section 2075, and a focus control section

2000. The region setting section 2010 sets a plurality of regions (evaluation blocks), each including a plurality of pixels, to an image acquired by an imaging section (corresponding to an imaging section 200 illustrated in FIG. 3 described later). The AF evaluation value calculation section 2030 calculates an AF evaluation value of each of the plurality of regions set. The invalid region setting section sets an invalid region that is a region, in the plurality of regions, determined to include a subject other than the target subject (a tissue in a narrow sense). The low contrast state determination section 2075 determines whether or not the target subject is in the low contrast state based on the AF evaluation value of a region, in the plurality of regions, other than the invalid region. The focus control section 2000 controls the in-focus object plane position based on the AF evaluation value. The focus control section 2000 implements the focus control varying depending on a determination result obtained by the low contrast state determination section.

Figure 3:
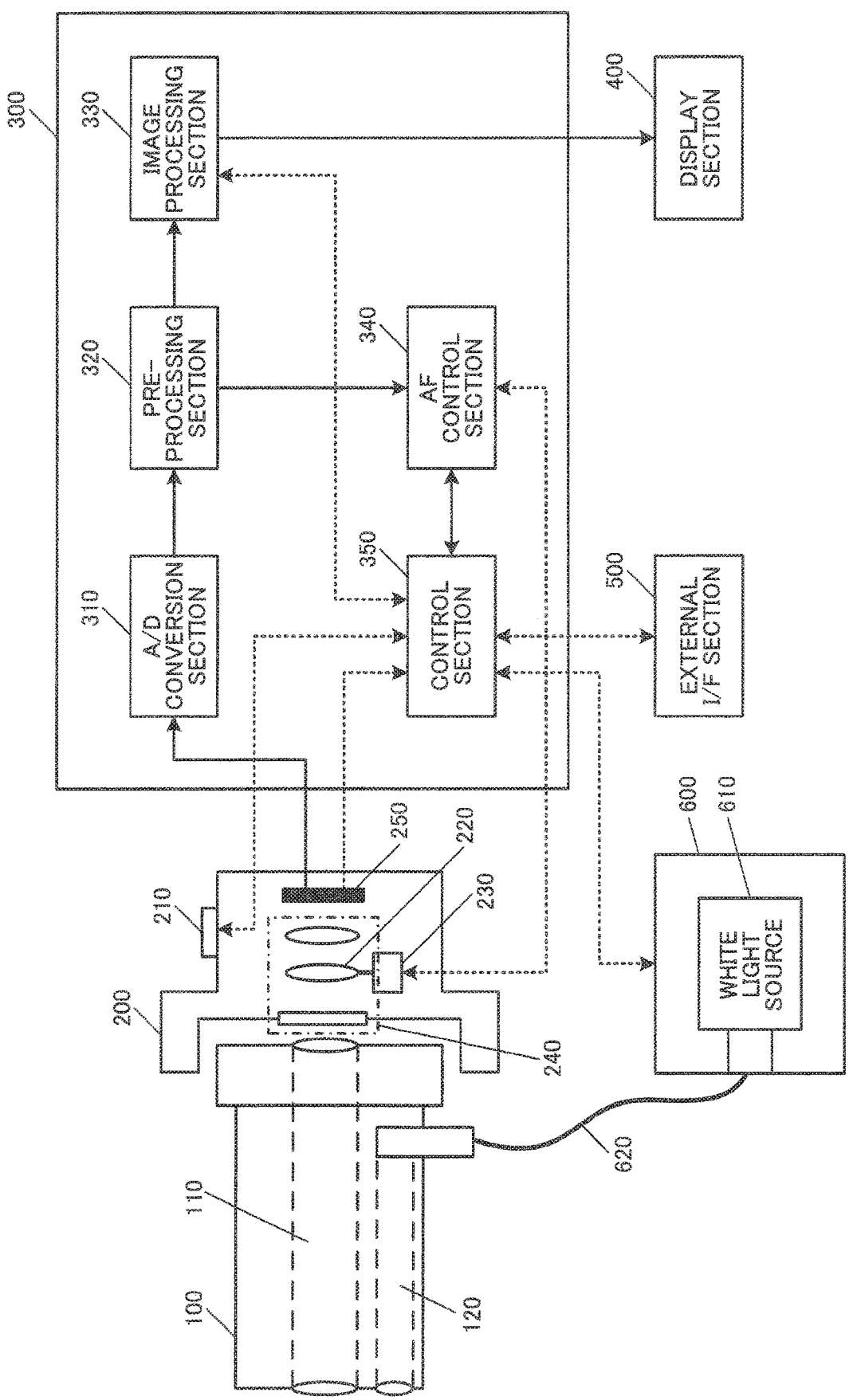
FIG. 3 illustrates a configuration example of the endoscope apparatus including the focus control device.

The in-focus object plane position as used herein represents a position of an object when a system, including an optical system (an objective lens system 240 in FIG. 3 described later in a narrow sense), an image plane (a plane of an image sensor 250 in FIG. 3), and an object (subject), is in an in-focus state. For example, as illustrated in FIG. 3, which will be referred to later, in a case where the image sensor 250 is fixed and a focus lens 220 in the optical system is movable, the in-focus object plane position is determined by determining the position of the focus lens 220. In this case, an image in which a subject positioned within a range of depth of field including the in-focus object plane position is focused is acquired.

With this configuration, determination of the low contrast state can be performed without using the invalid region (low contrast determination invalid block), and thus can be accurately performed. Thus, for example, whether or not the tissue is in the low contrast state can be appropriately determined, without being affected by the treatment tool, during the endoscopic procedure. The focus control section 2000 can implement focus control varying depending on whether or not the subject has been determined to be in the low contrast state. Specifically, a normal AF operation (for example, the AF operation based on wobbling) is performed when the subject is determined not to be in the low contrast state, and control for the low contrast state is performed when the subject is determined to be in the low contrast state. Thus, the normal AF operation can be prevented from being performed when the subject is in the low contrast state, whereby a risk of moving the focus lens in a wrong direction can be reduced. Furthermore, control for resolving the low contrast state or the like can be performed when the subject is determined to be in the low contrast state. Specifically, the control performed by the focus control section 2000 varies in accordance with whether a result of determination in S103 in FIG. 5A described later is Yes or No.

When the subject is determined to be in the low contrast state, the scanning using the focus lens described above may be performed. However, the scanning involves a large change in the blurring level of the image as described above, and thus results in a movie not suitable for monitoring. The scanning in the endoscope apparatus is particularly not preferable while a treatment performed by a user (physician) is in progress. The user is unaware of the scanning timing of the focus control device, and cannot control the scanning timing. Thus, the scanning is difficult to perform without hindering the monitoring by the user. Thus, in the present embodiment, a reset operation, different from the scanning, may be performed when the subject is determined to be in the low contrast state, as described in detail later with reference to FIGS. 5A and 5B.

The focus control device according to the present embodiment includes a memory (storage section) that stores therein information (for example, a program and various types of data) and a processor (a processing section 300 in FIG. 3, a processor including hardware) that operates based on the information stored in the memory. The processor performs processes including: a region setting process of setting a plurality of regions, each including a plurality of pixels, to an image acquired by the imaging section; an AF evaluation value calculation process of calculating the AF evaluation value of each of the plurality of regions set; an invalid region setting process of setting an region, in the plurality of regions, determined to include a subject other than the target subject to be an invalid region; a low contrast state determination process of determining whether or not the target subject is in the low contrast state based on the AF evaluation value of a region, in the plurality of regions, other than the invalid region; and a focus control of controlling the in-focus object plane position based on the AF evaluation value.

For example, the processor may have functions of sections each implemented by individual hardware, or the functions of sections implemented by integrated hardware. The processor may be a central processing unit (CPU), for example. Note that the processor is not limited to the CPU. Various other processors such as a graphics processing unit (GPU) or a digital signal processor (DSP) may also be used. The processor may be a hardware circuit that includes an application specific integrated circuit (ASIC). The memory may be a semiconductor memory (e.g., SRAM or DRAM), or may be a register. The memory may be a magnetic storage device such as a hard disk drive (HDD), or may be an optical storage device such as an optical disc device, for example. For example, the memory stores a computer-readable instruction, and the function of each section of the focus control device is implemented by causing the processor to perform the instruction. The instruction may be an instruction set that is included in a program, or may be an instruction that instructs the hardware circuit included in the processor to operate.

An operation according to the present embodiment is implemented as follows for example. The processor performs a process of setting a plurality of regions to an acquired image, and stores information on the plurality of regions in the memory. The processor reads the information on the plurality of regions from the memory, obtains the AF evaluation value (block AF evaluation value) of each of the regions, and stores the values in the memory. The processor reads the information on the plurality of regions from the memory, sets the invalid region based on the information (a feature amount of a pixel in a narrow sense as described later) on each region, and stores setting information on the invalid region in the memory. The processor reads the setting information on the invalid region and the AF evaluation value from the memory, determines whether or not the subject is in the low contrast state, and stores the determination result in the memory. The processor reads the AF evaluation value from the memory to control the in-focus object plane position. In this process, the control is performed while taking the result of the low contrast state determination read from the memory into consideration. Specifically, the in-focus object plane position may be controlled by a process of outputting a control signal to a mechanism (a focus lens driving section 230 in FIG. 3) that drives the focus lens.

The sections of the focus control device according to the present embodiment are implemented as modules of a program operating on a processor. For example, the region setting section is implemented as a region setting module that sets a plurality of regions, each including a plurality of pixels, to an image acquired by the imaging section. The AF evaluation value calculation section is implemented as an AF evaluation value calculation module that calculates an AF evaluation value of each of the plurality of regions set. The invalid region setting section is implemented as an invalid region setting module that sets a region, in the plurality of regions, determined to include a subject other than a target subject to be an invalid region. The low contrast state determination section is implemented as a low contrast state determination module that determines whether or not the target subject is in the low contrast state based on the AF evaluation value of a region, in the plurality of regions, other than the invalid region. The focus control section is implemented as a focus control module that controls the in-focus object plane position based on the AF evaluation value.

1.2 Overview of in-Focus Direction Determination Process

An impact of the subject other than the target subject on the low contrast state determination is described above. Note that the subject other than the target subject also has an impact on the focusing operation, that is, a result of determining the in-focus direction through wobbling. For example, contrast AF, with which a region with a higher contrast is brought into focus, might result in a treatment tool brought into focus instead of the tissue that is supposed to be brought into focus.

In this context, a desired subject can be accurately brought into focus with a method described in JP-A-2006-245792, featuring designation, made by the user, of a subject serving as an obstacle. However, a status of an obstacle in the captured image might frequently change under a given circumstance. In such a case, a large operation load is imposed on the user required to designate the obstacle each time the change occurs.

For example, during an endoscopic procedure, such as a laparoscopic surgery, a treatment tool is inserted into the body together with a scope (imaging section), and the treatment is performed on a tissue using the treatment tool. The treatment tool is used for a treatment, and thus is frequently moved by a user (a doctor, a physician). For example, a membranous tissue is pulled up using forceps, or a tissue immobilized with forceps is ablated using an electrocauter. As a result, the size and the position of the treatment tool in the captured image frequently change. Thus, a region of the obstacle in the captured image frequently changes, rendering the manual designation by the user extremely cumbersome.

In view of this, the system may perform a process of lowering the level of contribution of the region of the obstacle in the captured image to the AF control (process of excluding the region from the AF control in a narrow sense), whereby the target subject can be appropriately brought into focus.

Thus, the focus control device according to the present embodiment includes a direction determination section 2040 that implements a direction determination process of obtaining a direction determination result for each region in some or all of the plurality of regions set, by determining whether a target focusing position that is a target of the in-focus object plane position is on a NEAR side or a FAR side relative to a reference position. The focus control section 2000 (processor) determines the in-focus direction by performing weighted comparison between NEAR area information, indicating an area of a region with a determination result NEAR, and FAR area information, indicating an area of a region with a determination result FAR, based on the direction determination result and weight information. Then, the focus control section 2000 may control the in-focus object plane position based on the in-focus direction thus determined.

Note that NEAR and FAR each indicate the direction of the target focusing position relative to the reference position. The result NEAR is obtained when the target focusing position is closer to the imaging section 200 (the optical system and the image sensor 250) than the reference position is. The result FAR is obtained when the target focusing position is farther from the imaging section 200 than the reference position is. When the in-focus object plane position can be controlled based on the position of the focus lens 220 as in the example illustrated in FIG. 3, the in-focus object plane position can be controlled to move toward the NEAR side with the position of the focus lens 220 moved toward the near side, and can be controlled to move toward the FAR side with the position of the focus lens 220 moved toward the far side.

The weighted comparison is a process of comparing the NEAR area information and the FAR area information after weighting using the weight information. The weight information is at least one of first weight information indicating a level of contribution of each of a plurality of regions to the weighted comparison and second weight information indicating a level of contribution of the NEAR area information and the FAR area information to the weighted comparison. In other words, the weight information according to the present embodiment may be a weight used for calculating the NEAR area information (or the FAR area information or both) or may be a weight of the NEAR area information (or the FAR area information or both) itself.

With this configuration, the target subject can be brought into focus without requiring the user to perform a cumbersome operation. In particular, the configuration can provide an endoscope apparatus having an AF control function with which the target subject can be brought into focus without requiring the user to perform a cumbersome operation in various possible scenes during the endoscopic procedure. Specifically, appropriate AF control can be achieved due to the following three points.

1. In the present embodiment, the direction of moving the in-focus object plane position is determined based on the area information. The area information is determined based on the direction determination result (NEAR or FAR). Once the direction determination result is acquired based on the AF evaluation value (contrast value), the magnitude of the AF evaluation value of each region contributes to none of the processes thereafter. Generally, the treatment tool has a higher contrast than tissues. Thus, in normal contrast AF, a region including a treatment tool that has been failed to be detected is likely to have a large impact when used in the AF control. In the method according to the present embodiment, the in-focus direction is determined by area information comparison (weighted comparison). Thus, each region (evaluation block) is only worth a single vote regardless of the AF evaluation value of the subject, whereby the impact of the treatment tool can be limited.

2. In the present embodiment, the weight of each region for obtaining the area information (the weight of each region with a determination result NEAR for obtaining the NEAR area information in a narrow sense) can be set by using the first weight information. Thus, as described later with reference to FIG. 16, when a target region in the image can be identified, the target region can be brought into focus with priority.

3. In the present embodiment, the second weight information is used so that the NEAR area information and the FAR area information are not simply compared but are weighted to be compared. For example, NEAR area information $S_N$ and FAR area information $S_F$ can be compared to determine whether or not the following Formula (1) is satisfied instead of determining whether or not $S_N > S_F$ is satisfied.

$$M \times S_N > S_F \qquad (1)$$

where M represents the second weight information.

This Formula (1) can be converted into the following Formula (2) with M substituted with (1−Th)/Th, $$S_N/(S_N \pm S_F) > Th \qquad (2).$$

The left side in this Formula (2) corresponds to a ratio nearRatio of a NEAR block described later, and thus the weight information (second weight information) according to the present embodiment may be threshold TH_NEAR for determining the in-focus direction. As described later with reference to FIG. 14, the threshold TH_NEAR serves as a parameter for adjusting an in-focus position (the in-focus object plane position at the point when the focusing operation is completed). Thus, with the second weight information, the in-focus position can be flexibly adjusted.

The present embodiment is described in detail below. First of all, a system configuration example of a focus control device according to the present embodiment and an endoscope apparatus including the focus control device is described. Then, an overview of the AF control according to the present embodiment is described. In the overview of the AF control, a specific example of a reset operation performed when the subject is determined to be in the low contrast state is also described. After that, a specific example of the focusing operation and some modifications are described.

An apparatus (electronic apparatus) including the focus control device according to the present embodiment is not limited to the endoscope apparatus and may be any other apparatus. For example, an apparatus such as a digital still camera, a video camera, or a mobile phone may include the focus control device according to the present embodiment. Also in such a case, flexible AF control can be achieved with the impact of an obstacle limited and without requiring the user to go through a cumbersome operation.

2. SYSTEM CONFIGURATION EXAMPLE

The endoscope apparatus including the focus control device according to the present embodiment is described with reference to FIG. 3. The endoscope apparatus according to the present embodiment includes a rigid scope 100 that is inserted into a body, the imaging section 200 that is connected to the rigid scope 100, a processing device 300, a display section 400, an external I/F section 500, and a light source section 600.

The light source section 600 includes a white light source 610 that emits white light, and a light guide cable 620 that guides the light emitted from the white light source 610 to the rigid scope. The rigid scope 100 includes a lens system 110 that includes an imaging lens, a relay lens, an eyepiece, and the like, and a light guide section 120 that guides the light emitted from the light guide cable 620 to the end of the rigid scope. The imaging section 200 includes the objective lens system 240 that forms an image of the light emitted from the lens system 110. The objective lens system 240 includes the focus lens 220 that adjusts the in-focus object plane position. The imaging section 200 also includes the image sensor 250 that photoelectrically converts the reflected light focused by the objective lens system 240 to generate an image, the focus lens driving section 230 that drives the focus lens 220, and an autofocus (AF) start/stop button 210 that controls AF start/stop. The focus lens driving section 230 is a voice coil motor (VCM), for example.

The image sensor 250 has a structure in which a plurality of pixels are arranged in a two-dimensional array, and R, G, and B color filters are disposed in a Bayer array on a pixel basis. Alternatively, an image sensor that utilizes a complementary color filter, a stacked image sensor that is designed so that each pixel can receive light having a different wavelength without using a color filter, and a monochrome image sensor that does not utilize a color filter may be employed as long as the subject can be captured to obtain an image.

The processing section 300 includes an A/D conversion section 310, a pre-processing section 320, an image processing section 330, an AF control section 340, and a control section 350. The A/D conversion section 310 converts analog signals sequentially output from the image sensor 250 into digital images and sequentially outputs the digital images to the pre-processing section 320. The pre-processing section 320 performs image processing including white balance, an interpolation process (demosaicing process), and the like on the images output from the A/D conversion section 310, and sequentially outputs the resultant images to the image processing section 330 and the AF control section 340. The details of the AF control section 340 are described later. The image processing section 330 performs image processing including color conversion, gray scale conversion, edge enhancement, a scaling process, a noise reduction, and the like on the images output from the pre-processing section 320, and sequentially outputs the resultant images to the display section 400. The display section 400 is a liquid crystal monitor for example, and displays the image sequentially output from the image processing section 330.

The control section 350 is connected to the external I/F section 500, the image processing section 330, the AF control section 340, the image sensor 250, the AF start/stop button 210, and the like to exchange a control signal. The external I/F section 500 is an interface that allows the user to perform an input operation on the endoscope apparatus, for example. For example, the external I/F section 500 includes a mode button for switching the AF mode, a setting button for setting the position and the size of the AF area, an adjustment button for adjusting image processing parameters, and the like.

Figure 4:
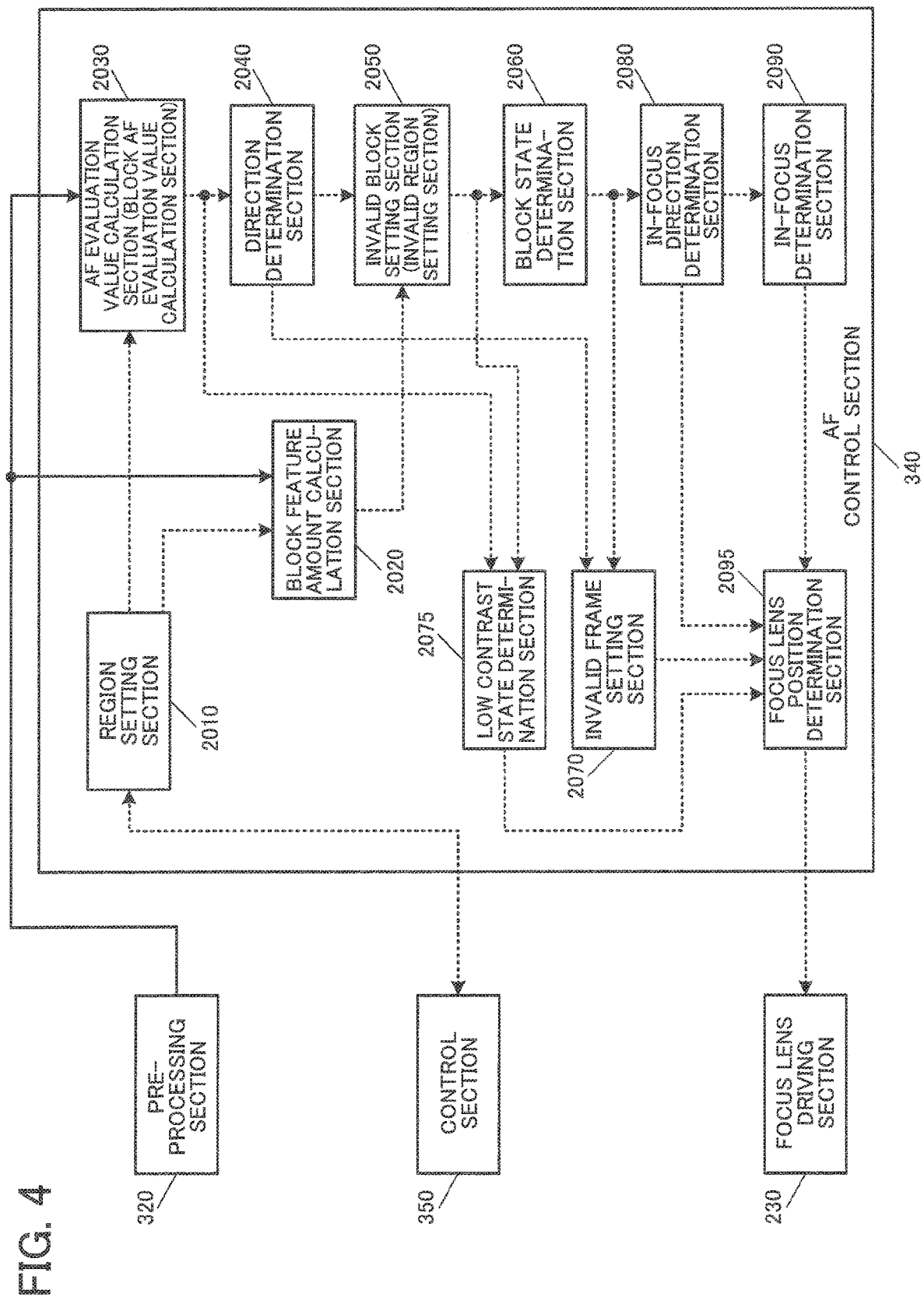
FIG. 4 illustrates a configuration example of an AF control section.

As illustrated in FIG. 4, the AF control section 340 includes, for example, the region setting section 2010, a block feature amount calculation section 2020, the AF evaluation value calculation section 2030, the direction determination section (block direction determination section) 2040, the invalid block setting section (invalid region setting section) 2050, a block state determination section 2060, an invalid frame setting section 2070, the low contrast state determination section 2075, an in-focus direction determination section 2080, an in-focus determination section 2090, and a focus lens position determination section 2095.

The region setting section 2010 sets regions, used for the AF, to the captured image. The regions may include both AF regions and evaluation blocks. The block feature amount calculation section 2020 calculates a feature amount for each evaluation block. The AF evaluation value calculation section 2030 calculates an evaluation value, used for the AF, for each evaluation block. The direction determination section 2040 determines the direction toward the target focusing position based on the AF evaluation value for each evaluation block. This direction determination result is information indicating NEAR or FAR in a narrow sense. The invalid block setting section 2050 sets an invalid block based on the feature amount. This invalid block includes an evaluation block not used in the in-focus direction determination and an evaluation block (low contrast determination invalid block) not used in the low contrast state determination. The block state determination section 2060 determines a block state that is a final direction determination result, based on history information on the direction determination result. The invalid frame setting section 2070 determines whether or not a process target frame is to be set as an invalid frame. The invalid frame is a frame not used in the in-focus direction determination. The low contrast state determination section 2075 determines whether or not the current frame is in the low contrast state. The in-focus direction determination section 2080 determines the in-focus direction, that is, a movement direction of the in-focus object plane position (or the movement direction of the focus lens 220 corresponding to the movement direction). The in-focus determination section 2090 determines whether or not the in-focus state is achieved by the movement of the in-focus object plane position, that is, whether or not to terminate the focusing operation. The focus lens position determination section 2095 determines a position to which the focus lens is moved. Specifically, the position is determined based on the movement in the in-focus direction obtained (movement of the wobbling center position) and the movement (wobbling operation) for determining the direction.

Processes performed by the sections of the AF control section 340 are described in detail later. The focus control section 2000 in FIG. 2 corresponds to the in-focus direction determination section 2080, the in-focus determination section 2090, and the focus lens position determination section 2095. However, the configuration of the focus control section 2000 is not limited to this, and may include the block state determination section 2060, the invalid frame setting section 2070, and the like in FIG. 4. The focus control device according to the present embodiment may correspond to the AF control section 340. However, this should not be construed in a limiting sense, and various modifications may be made including a modification where the entire processing section 300 in FIG. 3 serves as the focus control device. The focus control device may be modified in various ways with the components partially omitted, or additional components provided. Various modifications may be made also on other configurations in FIG. 3 and FIG. 4.

3. OVERVIEW OF PROCESS PERFORMED BY AF CONTROL SECTION

Figure 5A:
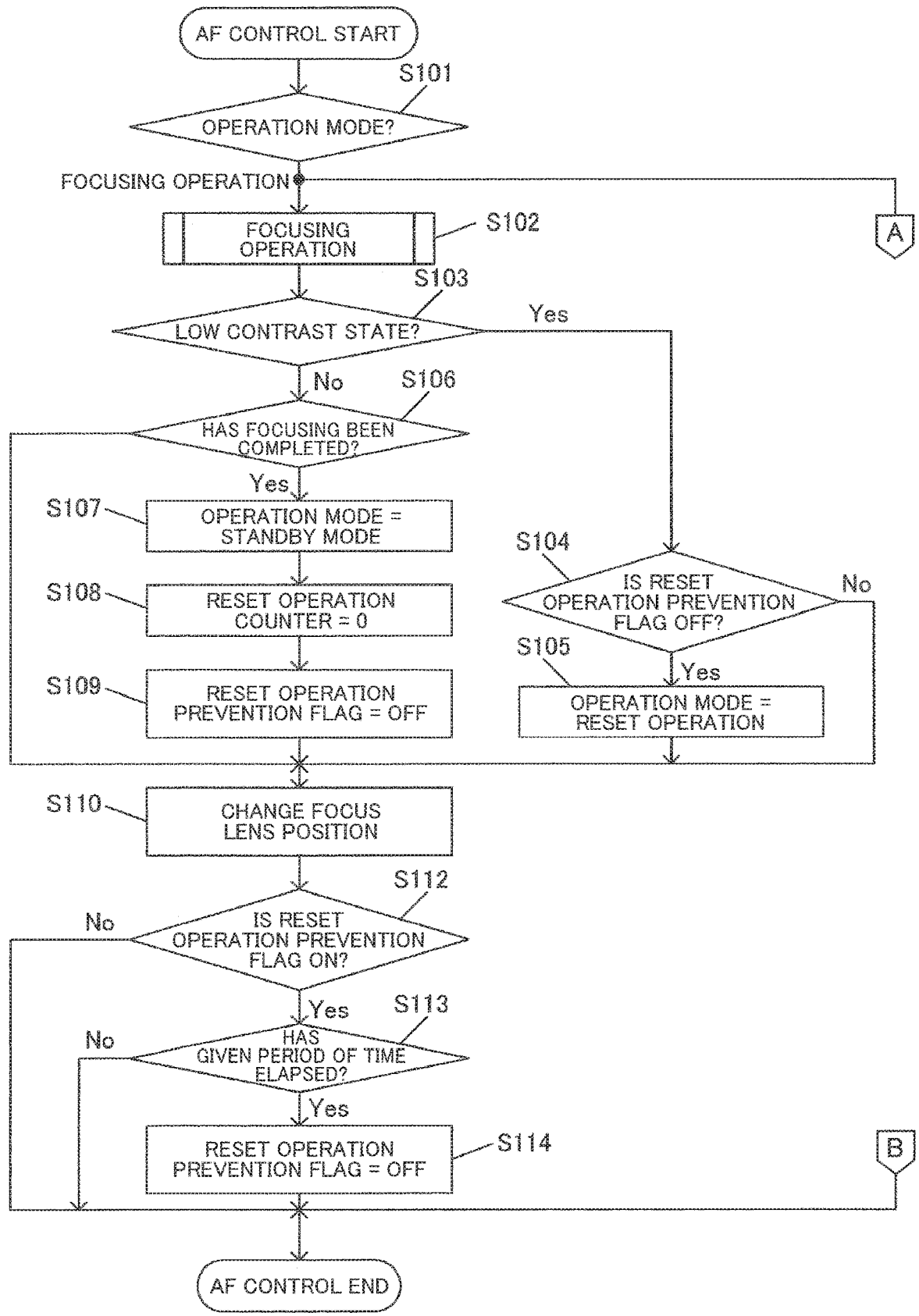
FIGS. 5A and 5B are flowcharts illustrating focus control.
Figure 5B:
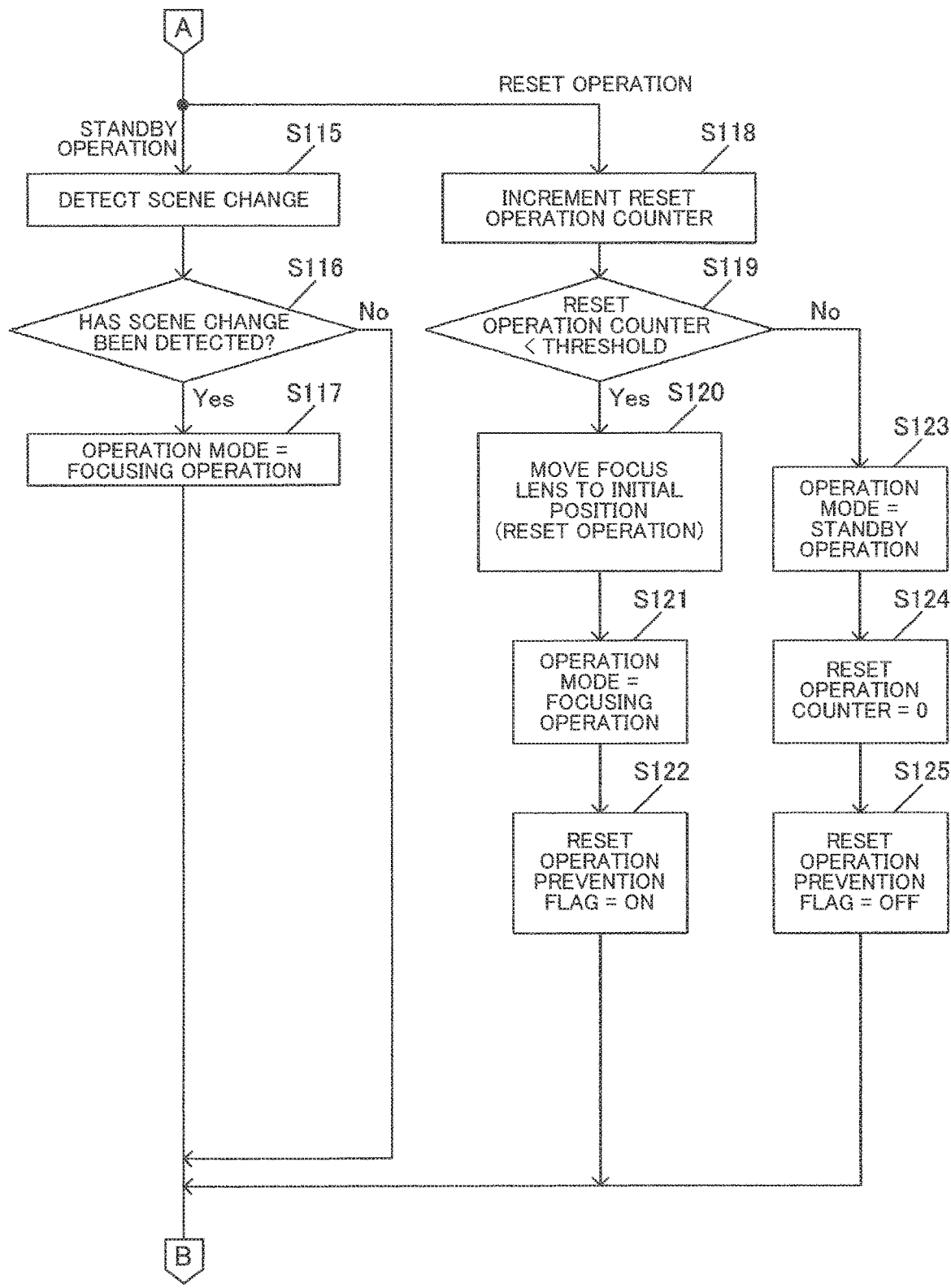

An overview of the AF control performed by the AF control section 340 according to the present embodiment is described with reference to FIGS. 5A and 5B. The AF control section 340 performs a process in FIGS. 5A and 5B on each frame while the AF is in progress.

<Focusing Operation>

When the AF starts as a result of the user operating the AF start/stop button 210, the operation mode of the AF control is set to be the focusing operation. When the AF control thus starts, the operation mode is first determined (S101). When the AF start/stop button 210 is operated, the operation mode is determined to be the focusing operation. When the focusing operation starts, the wobbling operation of the focus lens starts in synchronization with acquisition timings of images sequentially output from the A/D conversion section 310, and the focusing operation (the focusing operation in a narrow sense) is performed based on the images acquired during the wobbling operation (S102). The focusing operation is described in detail later with reference to FIG. 6 and the like.

Figure 6:
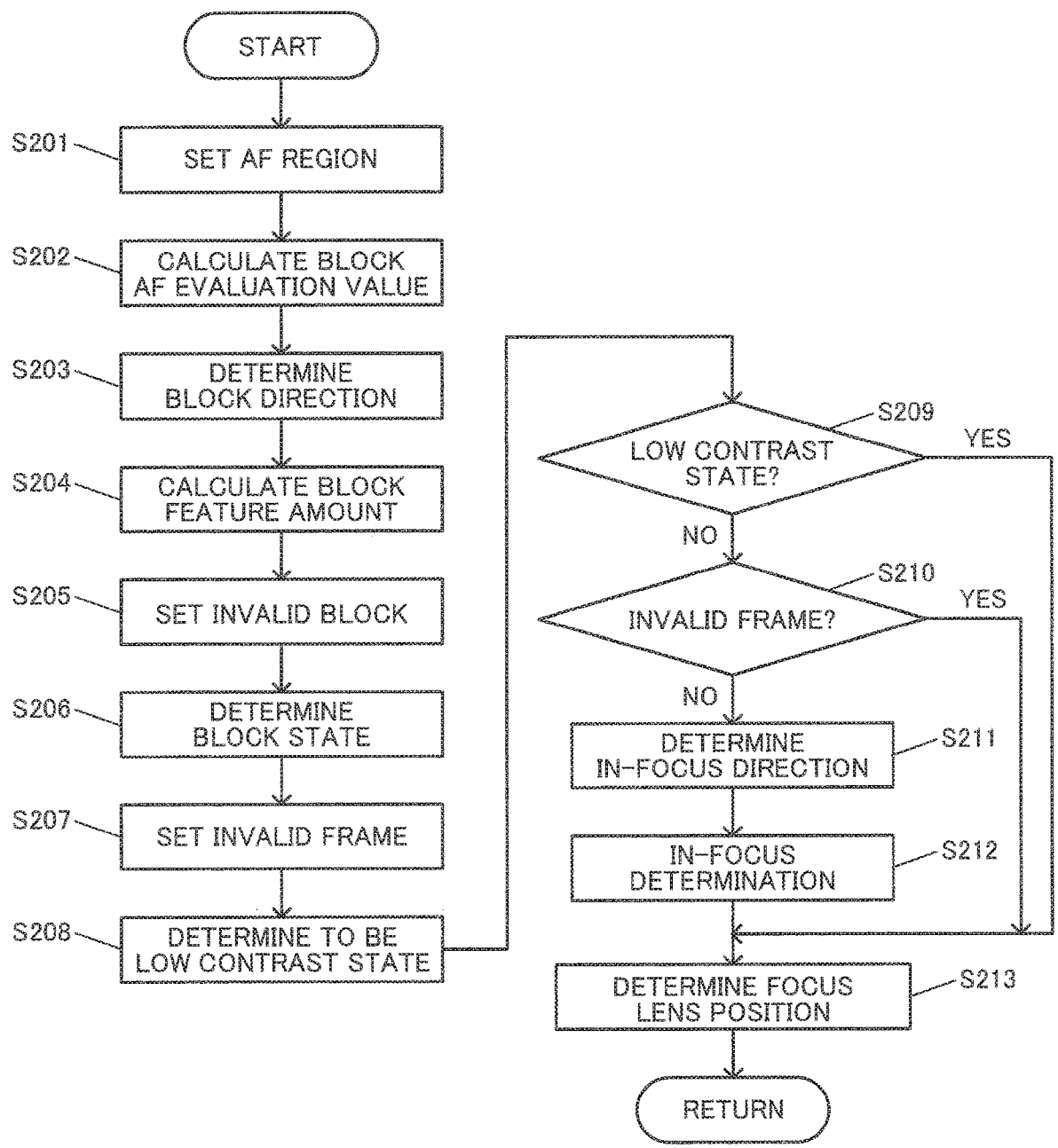
FIG. 6 is a flowchart illustrating a focusing operation.

As described later with reference to S208 in FIG. 6, the low contrast state determination is performed in the focusing operation in S102. Thus, whether or not the subject has been determined to be in the low contrast state is determined after the focusing operation (S103). When the determination result is the low contrast state (Yes in S103), whether a reset operation prevention flag is ON or OFF is determined (S104).

In the reset operation, the focus lens is moved to a given position, and thus the focus status (a level of blurring) changes. The reset operation prevention flag is for preventing the reset operation from being successively performed within a given time period. Thus, images not suitable for the monitoring can be prevented from being output at a high frequency.

When the reset operation prevention flag is OFF (Yes in S104), the operation mode is changed to the "reset operation" (S105). As a result, the determination result in S101 is a reset operation in the next frame, and thus the reset operation described later with reference to S118 to S125 is performed. When the reset operation prevention flag is ON (No in S104), the operation mode remains unchanged even when the subject is in the low contrast state.

When the subject is not in the low contrast state (No in S103), whether or not the focusing is completed is determined (S106) based on a result of the in-focus determination (S212 in FIG. 6 described later) performed in the focusing operation in S102. When the focusing has been completed (Yes in S106), the operation mode is changed to "standby operation" (S107), the reset operation counter is reset to 0 (S108), and the reset operation flag is turned OFF (S109). The focus lens position is changed (S110). This focus lens position is an in-focus position described later with reference to FIG. 18. When the focusing operation has not been completed (No in S106), the focus lens position is changed (S110). The focus lens position to be set as a result of the changing has been determined in the determination process for the focus lens position described later with reference to FIG. 20.

The reset operation counter is a counter for counting the number of reset times. Generally, when the reset operation is performed, the low contrast state should be resolved so that the in-focus direction can be determined. However, the in-focus direction cannot be determined by the reset operation in some scenes, such as a situation where an image of the low contrast subject is being captured. Thus, in the present embodiment, the number of reset operation times is measured using the counter, and the reset operation is determined to be ineffective when the value of the counter exceeds a threshold. A specific process performed in such a situation is described later with reference to S123 to S125. When the process has reached S108, the focusing has been completed, that is, the AF control has been successfully completed. Thus, the reset operation counter is reset to 0.

The focus lens position is changed (S110) also when a result of S104 is No and after the process in S105. The process proceeds to the determination in S104 when the subject has been determined to be in the low contrast state (Yes in S103), and thus the wobbling center position remains unchanged. Thus, the process in S110 corresponds to the wobbling operation (an operation of moving the focus lens by a wobbling amount relative to the wobbling center position). After the process in S110, whether the reset operation prevention flag is ON or OFF is determined (S112). When the result of this determination is OFF (No in S112), the AF control is terminated. When the result of this determination is ON (Yes in S112), whether or not a given period of time has elapsed after the reset operation prevention flag has been turned ON is determined (S113). When the given period of time has not elapsed yet (No in S113), the AF control is terminated. When the given period of time has elapsed (Yes in S113), the reset prevention flag is turned OFF, and then the AF control is terminated.

As described later with reference to S122, the reset operation prevention flag is turned ON when the reset operation has been performed. Thus, after the reset operation is performed through the processes in S112 to S114, the reset operation can be prevented from being performed for a given period of time. Thus, the reset operation can be prevented from being successively performed when the subject is maintained in the low contrast state, whereby the AF control can be performed with no stress on the user.

<Standby Operation>

When the operation mode is set to be a standby operation, the standby operation is performed based on the determination in S101. When the standby operation starts, the AF control section 340 performs a scene change detection process (S115). For example, the AF control section 340 uses images sequentially output from the pre-processing section 320 to perform the scene change detection process by monitoring changes in the color, the luminance, or the AF evaluation value in an image, or the movement in the image.

Next, whether or not a scene change has been detected is determined (S116). When the scene change has not been detected (No in S116), the AF control is terminated. After the transition to the standby operation due to the focusing completion (when the process in S107 has been performed), the in-focus state can be maintained without moving the focus lens as long as the scene does not change. Thus, the focusing operation is not required. After the transition to the standby operation due to the reset operation being ineffective (when a process in S123 described later has been performed), the subject in the current scene is in the low contrast state that cannot be improved by the reset operation. Thus, the focusing operation should not be performed as long as the scene remains unchanged. In any case, after the transition to the standby operation, the standby operation should be maintained as long as the scene remains to be the same. Thus, the focus lens is not driven during the standby operation.

When the scene change has been detected (Yes in S116), the operation mode is changed to the "focusing operation", and the AF control is terminated. Thus, the focusing operation is performed in the next frame.

<Reset Operation>

When the operation mode is changed to the reset operation in S105, the reset operation is performed as a result of the determination in S101 for the next frame. When the reset operation starts, the reset operation counter is first incremented (S118).

Next, whether or not the value of the reset operation counter is smaller than the threshold is determined (S119). When the value of the reset operation counter is determined to be smaller than the threshold (Yes in S119), the focus lens is moved to an initial position (S120). For example, the initial position is a position around the middle of the NEAR end and the FAR end (the position at which any subject in a range from a near subject to a far subject can be somewhat brought into focus). The operation in S120 corresponds to the reset operation in a narrow sense. Then, the operation mode is changed to the "focusing operation" (S121), the reset operation prevention flag is turned ON (S122), and the AF control is terminated.

As described above, in a video camera or the like, when the subject is determined to be in the low contrast state (largely blurred state), control is performed to search for the in-focus position through the scanning using the focus lens. In an endoscope system, the doctor may frequently move the imaging section without being aware of the focus lens scanning timing of the AF control section. Thus, the AF control section 340 might perform the scanning operation while the doctor is moving the imaging section. As a result, motion blur or the like occurs to lead to an inaccurate calculation of the in-focus position, resulting in increased stress.

During the endoscopic procedure, the entire AF region is almost never occupied by a low contrast subject. Thus, the in-focus direction can be determined by wobbling, with the position of the focus lens reset to be the position at which any subject within a range from a near subject to a far subject can be somewhat brought into focus. All things considered, the tissue in the low contrast state (largely blurred state) can be accurately brought into focus through the reset operation illustrated in FIG. 6.

When the reset operation counter is equal to or larger than the threshold (No in S119), the operation mode is changed to the "standby operation" (S123). Then, the reset operation counter is reset to 0 (S124), the reset operation prevention flag is turned OFF (S125), and the AF control is terminated.

As described above, when the low contrast state determination section 2075 determines that the target subject is in the low contrast state, the focus control section 2000 (processor) performs the reset operation of moving the focus lens 220 to a given position, and controls the in-focus object plane position after the reset operation is performed.

The given position is a position excepted to enable the in-focus direction to be determined through the wobbling. Specifically, the given position is a position expected to make a range of variation of the AF evaluation value through the wobbling operation to be equal to or larger than a given value. The AF evaluation value is an index value indicating the focusing level. Thus, a position at which any subject within a range from a near subject to a far subject can be somewhat brought into focus may be set to be the "given position". The position may be a position around the middle of the near end point and the far end point for example.

Thus, when the subject is determined to be in the low contrast state, the reset operation can be appropriately performed. This method involves no movement (scanning) of the focus lens over a large range, whereby stress imposed on the user can be reduced.

After the reset operation is performed, the focus control section 2000 (processor) prevents the reset operation from being performed for a given period of time. Specifically, the reset operation prevention flag is provided and turned ON when the reset operation is performed (S122), and is turned OFF when a given period of time has elapsed after the reset operation was performed (S113, S114). The operation mode is set to be the "reset operation" when the reset operation prevention flag is OFF (S104, S105). Thus, the reset operation can be prevented through this flag management.

Thus, the reset operation can be prevented from being repeated within a short period of time. Thus, the focus lens position can be prevented from frequently changing, whereby stress on the user can be reduced. Specifically, the frequency of the reset operation can be limited to be no more than once in the "given period of time".

The focus control section 2000 (processor) performs a count process of counting the number of reset times indicating the number of times the reset operation has been performed, and puts the control on the in-focus object plane position in standby when the number of reset times reaches or exceeds a given threshold. Specifically, the number of reset times is counted with the reset operation counter incremented each time the reset portion process starts (S118). When the threshold is reached or exceeded (Yes in S119), the operation mode is set to be the "standby operation" (S124).

With this process, the reset operation can be prevented from being repeated in a scene where the subject is difficult to be brought into focus by the AF, whereby the AF control involving less stress on the user can be achieved. Thus, in the present embodiment, the frequency and the number of times of the reset operation are controlled so that the stress on the user can be reduced. After the reset operation, the standby operation is performed in the next frame, and the focusing operation can be performed when the scene changes to enable the focusing.

4. DETAIL OF FOCUSING OPERATION

Next, a focusing operation (S101) performed by the AF control section 340 is described in detail with reference to a flowchart in FIG. 6.

<AF Region Setting>

Figure 7:
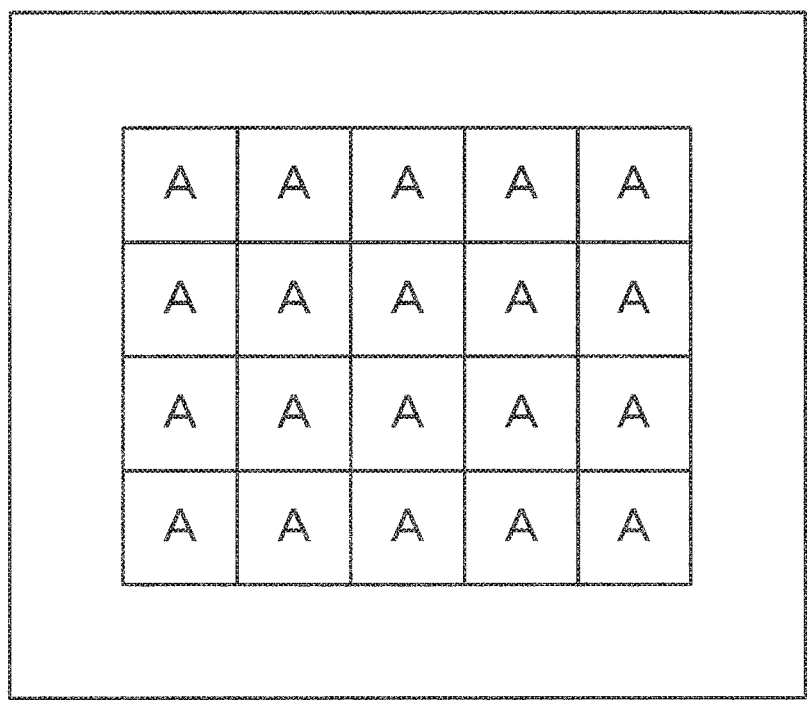
FIG. 7 illustrates an example of how a plurality of regions (evaluation blocks) are set.

When the operation starts, the region setting section (AF region setting section) 2010 first sets the AF region including a plurality of blocks on the image (S201). FIG. 7 illustrates an example of the AF region thus set. In FIG. 7, an outer rectangle represents the entire image, and each rectangle including the sign A represents an evaluation block that is a target of calculating the AF evaluation value, the feature amount, or the like as described later. In FIG. 7, a range surrounding all of the evaluation blocks serves as the AF region. In FIG. 7, total of 20 evaluation blocks, including five blocks in a lateral direction and four blocks in a vertical direction, are set to be in a center portion of image data.

<Block AF Evaluation Value Calculation>

The AF evaluation value calculation section 2030 calculates the block AF evaluation value (the AF evaluation value) of each evaluation block, based on a pixel value of the image data output from the pre-processing section 320 (S202). The block AF evaluation value increases as the focusing level of the subject in the block increases. For example, the block AF evaluation value is calculated as a sum of output values obtained as a result of applying a bandpass filter to each pixel in an image in each evaluation block.

<Block Direction Determination>

The direction determination section 2040 determines the target in-focus direction for each evaluation block from the block AF evaluation value of the evaluation block (S203). An example of the determination method is described with reference to FIG. 8A, with AfVal[N] representing the latest block AF evaluation value (in the current frame) output from the AF evaluation value calculation section 2030, and AfVal[N−1] and AfVal[N−2] respectively representing the block AF evaluation values output in the previous frame and in the frame immediately before the previous frame. The direction determination section 2040 calculates a block AF evaluation value change amount α with the following Formula (3).

$$\alpha = \{(AfVal[N] + AfVal[N-2])/2)\} - AfVal[N-1] \quad (3)$$

Figure 8A:
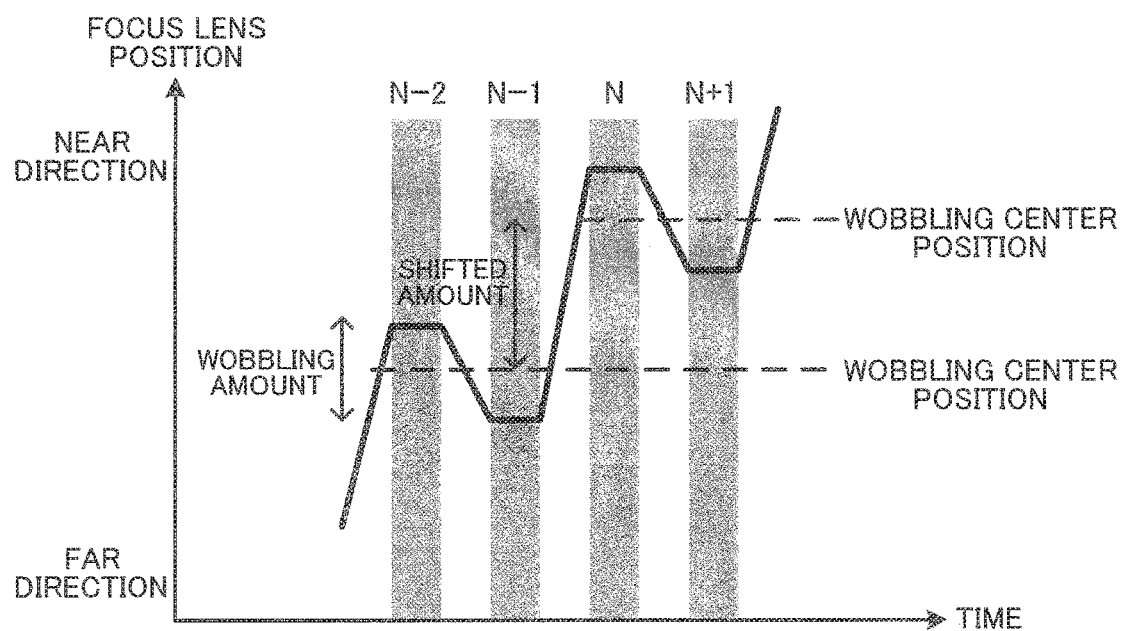
FIG. 8A is a diagram illustrating an example of how a focus lens according to an embodiment is controlled in a direction determination process.

Through this process, the in-focus direction can be accurately calculated with a shift operation performed together with the wobbling as illustrated in FIG. 8A (even when the amounts of the movement of the focus lens in the NEAR direction and in the FAR direction are not constant).

Comparison between the AF evaluation values obtained in the two frames in series with the focus lens moved as illustrated in FIG. 8A has the following problem. Specifically, the focus lens moves by an amount corresponding to the wobbling amount between N−2 and N1, but moves by an amount as a result of adding a shifted amount to the wobbling amount between N−1 and N. Thus, the lens movement amount varies among timings, and thus the direction cannot be stably determined.

Figure 8B:
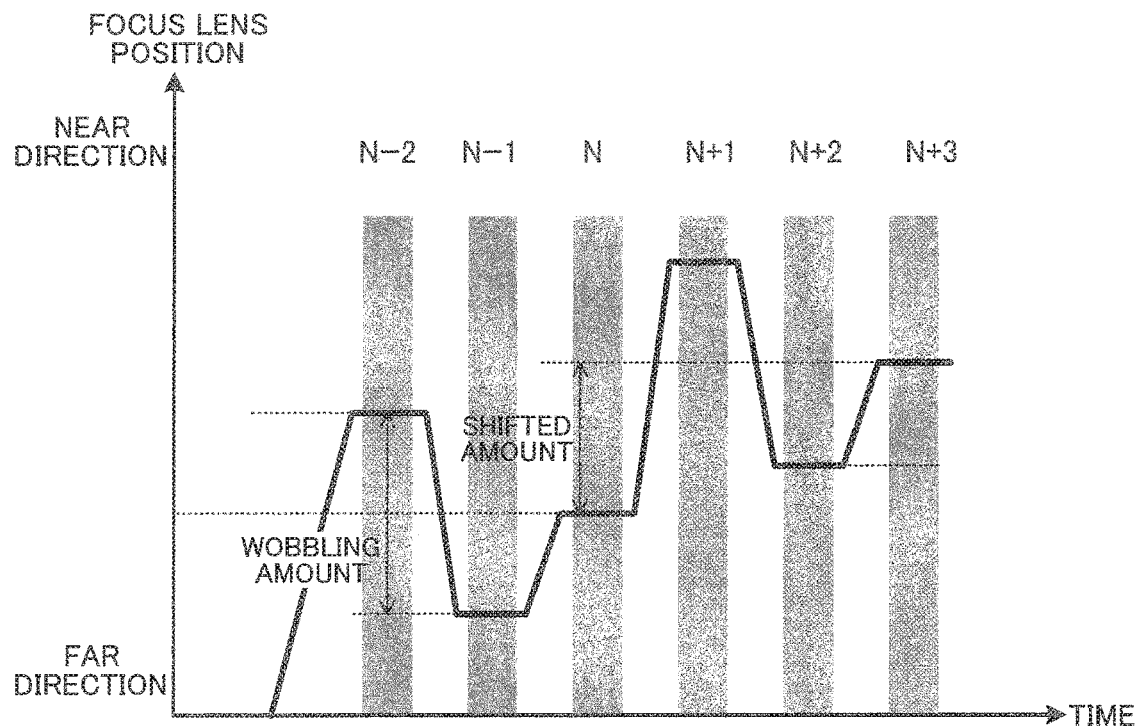
FIG. 8B is a diagram illustrating a conventional method.

FIG. 8B illustrates a general wobbling operation as a comparative example. In this case, the movement direction of the wobbling center position is determined by determining the target in-focus direction, with the AF evaluation values calculated in two frames (N−2 and N−1) and compared with each other in the Nth frame. In this process, a constant movement amount (amplitude) of the focus lens can be achieved for each direction determination process. Unfortunately, the method in FIG. 8B can only obtain a single direction determination result per three frames, and is difficult to achieve a high speed focusing operation and the like. For example, the direction determination result can be obtained in only two frames (N and N+3) within the range illustrated in FIG. 8B.

In view of this, Formula (3) described above is used so that a substantially stable lens movement amount can be achieved. For example, in the Nth frame, determination is performed for the movement of the focus lens between an average position between the Nth and the N−2th frames and the position in the N−1th frame. In the subsequent frame (N+1), the determination is performed for the movement of the focus lens between an average position between N+1 th and N−1 th frames and the position in the Nth frame. The amount of this movement is substantially the same as the movement amount in the Nth frame. The same applies to the subsequent frames.

With this configuration, the wobbling and the shift operation can be performed at the same time as illustrated in FIG. 8A, whereby the subject can be quickly brought into focus. Furthermore, the direction determination result can be obtained in each frame.

The value of the block AF evaluation value change amount α, obtained with Formula (3) described above, varies not only based on the blurring level, but also varies based on the luminance or the contrast of the subject. In this example, an index value representing the blurring level in each evaluation block is acquired, and thus components based on the luminance and the contrast of the subject are preferably removed. In the present embodiment, the block AF evaluation value change amount α obtained by Formula (3) described above is normalized to obtain a block AF evaluation value change rate β. Specifically, the following Formulae (4) and (5) may be used. In the present embodiment, the determination result is determined to be NEAR when the block AF evaluation value change rate β is a positive value, and is determined to be FAR when the block AF evaluation value change rate β is a negative value. Thus, when AfVal[N] is calculated from an image as a result of the movement of the focus lens in the NEAR direction, the following Formula (4) is used. When AfVal[N] is calculated from an image as a result of the movement of the focus lens in the FAR direction, the following Formula (5) is used. In the formulae, Ave(a, b, c) represents an average value of a, b, and c.

$$\beta = \alpha / \text{Ave}(\text{AfVal}[N], \text{AfVal}[N-1], \text{AfVal}[N-2]) \quad (4)$$

$$\beta = -1 * \alpha / \text{Ave}(\text{AfVal}[N], \text{AfVal}[N-1], \text{AfVal}[N-2]) \quad (5)$$

The block AF evaluation value change rate β obtained with Formula (4) or (5) descried above is a value obtained by normalizing the block AF evaluation value change amount α. Thus, a substantially constant value is obtained in accordance with the focusing level change range in the wobbling, regardless of the contrast and the brightness of the subject.

<Block Feature Amount Calculation>

The block feature amount calculation section 2020 calculates a feature amount of each evaluation block (such as color information, luminance information, a size of a bright spot) based on image data output from the pre-processing section 320 (S204). The calculation of the feature amount is implemented with a widely known method which will not be described in detail.

<Invalid Block Setting>

The invalid block setting section 2050 sets the invalid block based on the block AF evaluation value change rate β obtained in S203 and the block feature amount obtained in S204 (S205).

First of all, the invalid block setting section 2050 sets an evaluation block with an absolute value of the block AF evaluation value change rate β being outside a given range to be an invalid block. For example, the evaluation block satisfying |β|<first threshold or |β|>second threshold (>first threshold) is set to be an invalid block. A correct direction determination result cannot be obtained from a subject with an insufficient contrast or from a largely blurred image. In such a case, the block AF evaluation value change rate β is small.

A correct direction determination result cannot be obtained when a subject in the captured image changes due to the movement of the subject or the like, when the treatment tool suddenly enters the image, or when any of images used for calculating the block AF evaluation value change rate β involves motion blur. In such cases, the block AF evaluation value change rate β is large.

In view of this, an unreliable evaluation block involving an excessively small or large block AF evaluation value change rate β can be set to be the invalid block, whereby a highly accurate in-focus direction determination process can be achieved.

The invalid block setting section 2050 detects an evaluation block, a high luminance portion, and a dark portion occupied by an object other than the tissue such as the treatment tool (a silver color or a black color) and a bright spot, and the like, from the block feature amount (such as color information, luminance information, and the size of the bright spot) of the evaluation block, and sets such an evaluation block to be the invalid block. With such a process, the block including no tissue or a block with an unreliable block direction determination result can be set to be the invalid block.

<Block State Determination>

Then, the block state determination section 2060 determines the block state based on the block direction determination result obtained in S203 and the invalid block setting result obtained in S205 (S206).

First of all, when there is an invalid block in the current frame or the two previous frames, the block direction determination result is unreliable, and thus the block state of the current frame is set to be invalid. This is because the block direction determination is performed using the block AF evaluation values in the current frame and the two previous frames as described above with reference to Formula (3).

In the present embodiment, the block state is updated when the block direction determination result remains to be the same for a threshold period or mode. Otherwise, the block state of the previous frame is maintained. Thus, the reliability of the block state can be improved and can be prevented from frequently changing.

Figure 9:
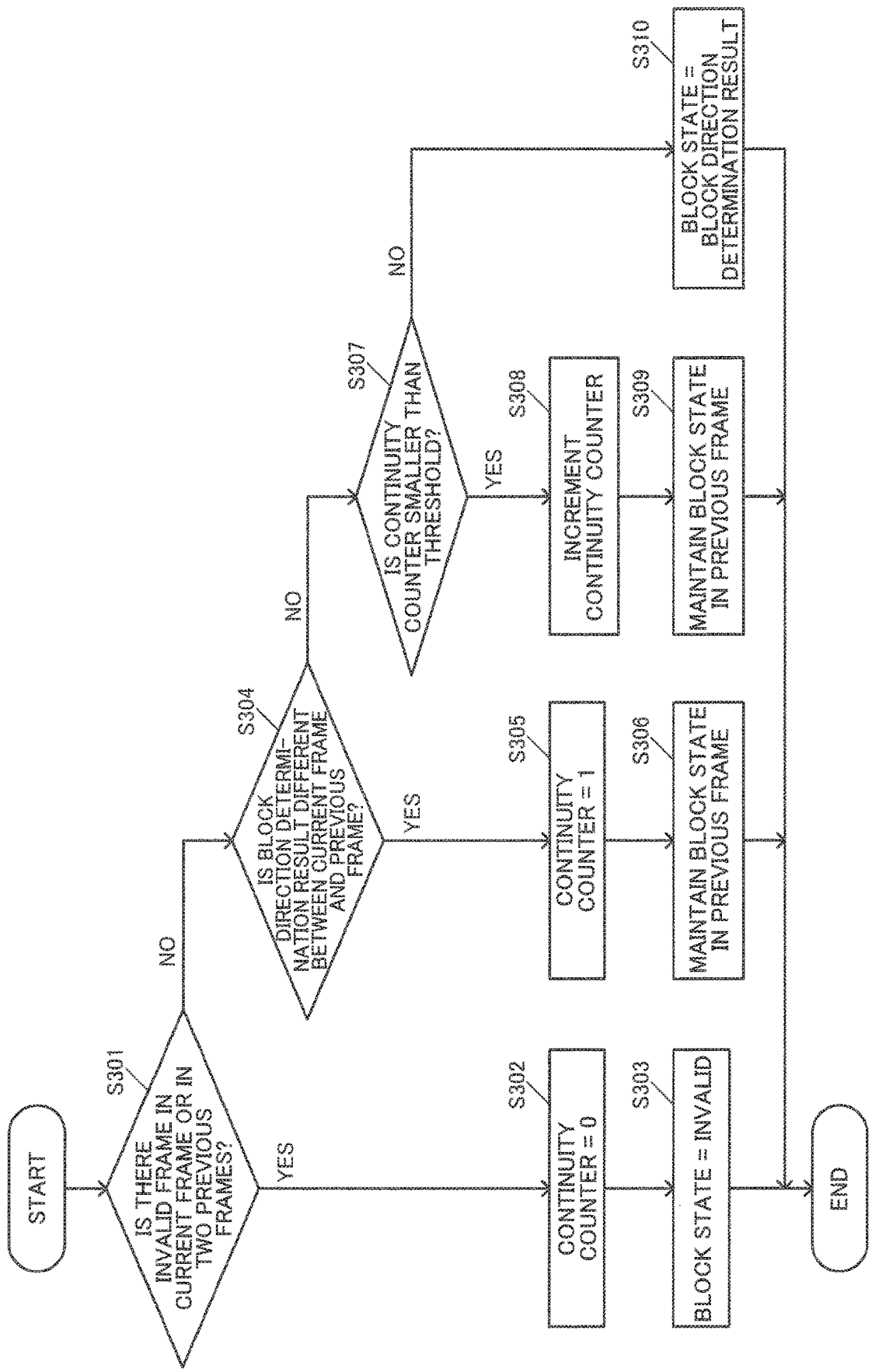
FIG. 9 is a flowchart illustrating a block state determination process.

FIG. 9 is a flowchart illustrating a process performed by the block state determination section 2060. When this process starts, first of all, it is determined whether or not there is an invalid block in the current frame or in two previous frames (S301). When a result of the determination in S301 is Yes, a continuity counter is set to be 0 (S302), and the block state is set to be the invalid block (S303). The continuity counter represents the number of times the same direction determination result was obtained. When there is an invalid block in the two previous frames, the direction determination result (NEAR or FAR) for the current frame is unreliable. Thus, the continuity counter remains to be 0 regardless of the direction determination result in the current frame in S302.

When a result of the determination in S301 is No, whether or not the direction determination result is different between the current frame and the previous frame (frame one before the current frame) is determined (S304). When the result of the determination in S304 is Yes, it means that the direction determination result has changed. Thus, the continuity counter is set to be 1 because the same direction determination result is not maintained (S305). Furthermore, the block state in the previous frame is maintained because the value of the continuity counter does not exceed the threshold (S306).

When the result of the determination in S304 is No, there is no invalid block in the two previous frames, and thus the same direction determination result is maintained. Thus, the process of determining whether the value of the continuity counter is smaller than the threshold (for example, 2) is performed (S307). When the result of the determination in S307 is Yes, the same direction determination result is maintained, and thus the continuity counter is incremented (S308). However, the block state in the previous frame is maintained because the direction determination result is not maintained long enough (S309).

When the result of the determination in S307 is No, the same direction determination result is maintained long enough. Thus, the block state is changed due to the direction determination result in the current frame (S310).

Figure 10:
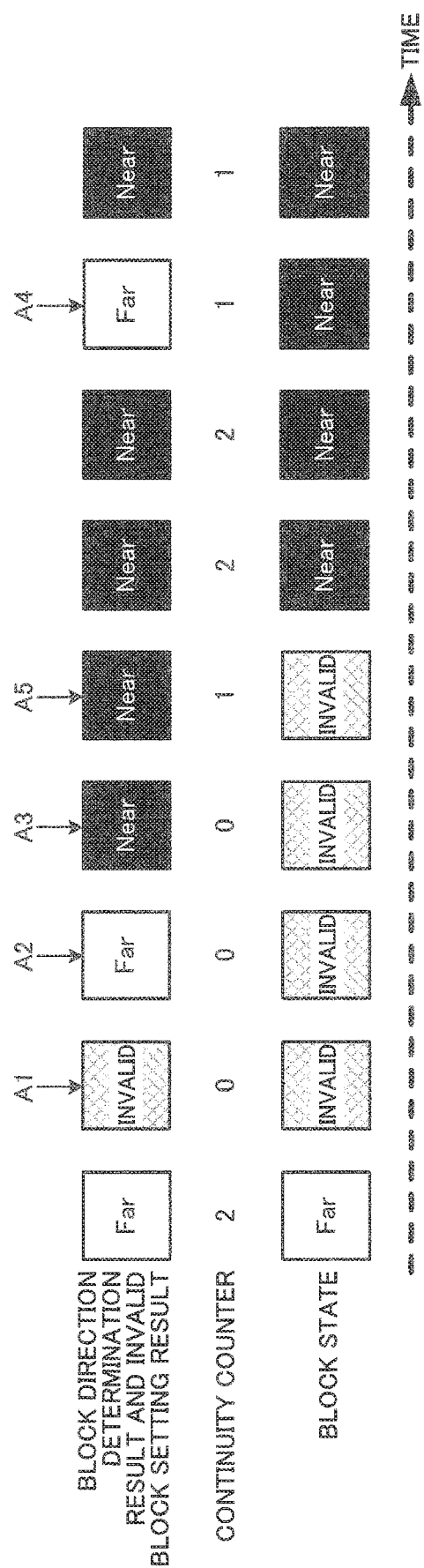
FIG. 10 illustrates a specific example of how a block state changes over time.

FIG. 10 illustrates a specific example. In FIG. 10, a given evaluation block in a plurality of evaluation blocks is set as a target. The direction determination result in S203 and the invalid block setting result in S205 are illustrated in the upper stage, and the block state is illustrated in the lower stage.

The target evaluation block is set to be the invalid block in a frame A1 in FIG. 10, and the block state in the frame is also set to be invalid. The direction determination result is FAR in a frame A2, and is NEAR in a frame A3. Still, the block states in these frames are invalid block, because there is an invalid block in the two previous frames.

In a frame A4, the direction determination result is switched to FAR from NEAR, but the continuity counter is 1 because the result FAR is not maintained. In this example, the threshold is 2, and thus the continuity counter≤threshold is satisfied, whereby the previous frame is maintained in the frame A4. Thus, the block state NEAR is maintained, even when the direction determination result is FAR.

The same applies to a frame A5. There is no invalid block in the two previous frames from the frame A5. The continuity counter in the frame A5 is 1 because the continuity counter in the previous frame A3 is 0. Thus, continuity counter≤threshold is satisfied, whereby the invalid block from the previous frame (A3) is maintained in the frame A5.

<Invalid Frame Setting>

Next, the invalid frame setting section 2070 sets the invalid frame (S207). The image in the frame determined to be an invalid frame is not suitable for determining the in-focus direction, and results in the direction determination result with a low reliability. Thus, the in-focus object plane position is not moved based on such a direction determination result. Specifically, only the wobbling operation is performed, with the focus lens moved by an amount corresponding to the wobbling amount without moving the center position (without moving the focus lens by an amount corresponding to the shift amount) for the wobbling operation. The invalid frame is set when mist is detected, or when an invalid subject is detected.

Thus, the invalid frame setting section 2070 first detects the mist based on the direction determination result for each evaluation block output from the direction determination section 2040. As described later, the mist is detected while taking the continuity of the direction determination result among frames into consideration, and thus the block state output from the block state determination section 2060 is not involved in the detection.

The mist produced during the endoscopic procedure might lead to a failure to accurately determine the block detection, and thus might result in an unstable focusing operation. The mist is produced only when the user uses the treatment tool such as an electrocauter to perform a treatment. Thus, the subject is somewhat in focus while the mist is being produced. Thus, the focusing operation may be interrupted when the mist is detected, so that the treatment performed by the user can be prevented from being affected.

Figure 11:
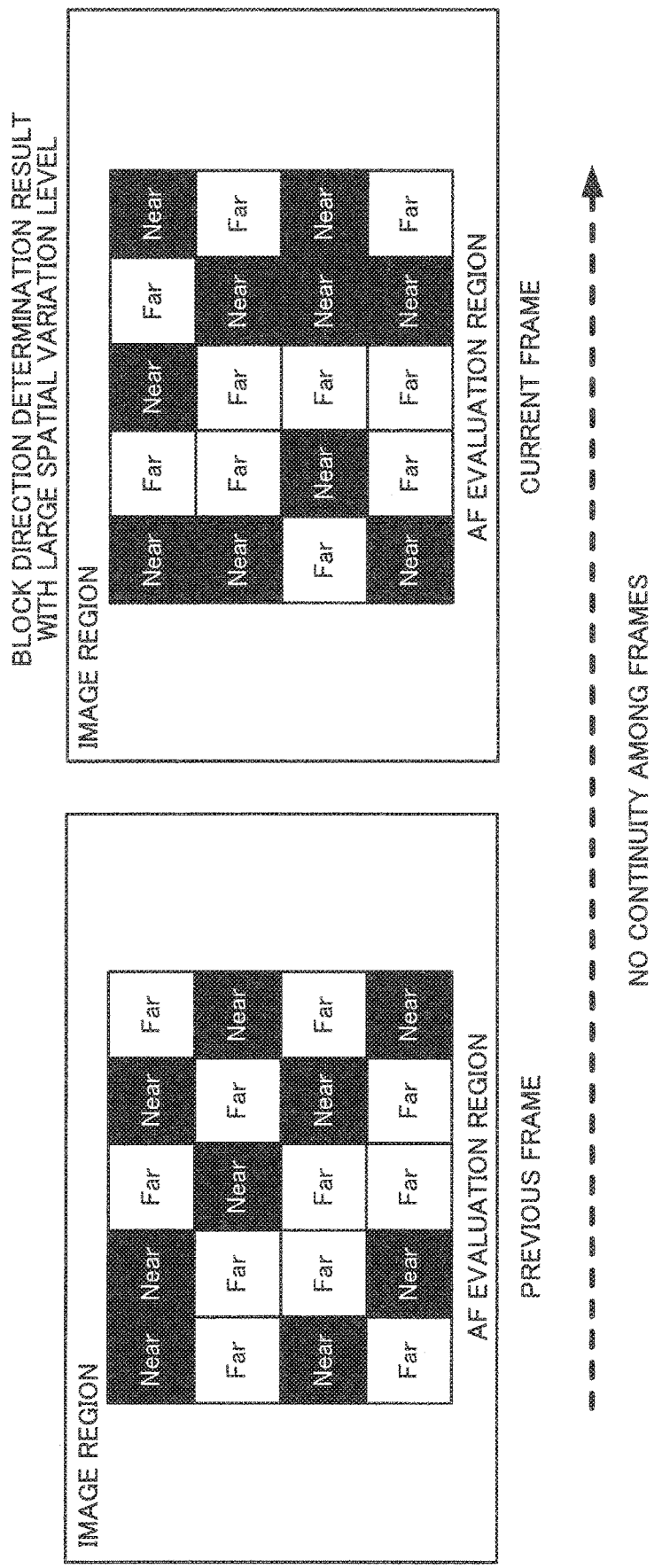
FIG. 11 illustrates an invalid frame setting process based on a direction determination result.

The mist is detected based on the level of variation of the direction determination result among frames, and among evaluation blocks in a frame. When the mist is produced, the density of the mist on the image largely fluctuates, and the distribution of the variation largely changes within a short period of time. As a result, the AF evaluation value similarly changes largely. Thus, the block direction determination result makes a large temporal and special change in FIG. 11. Thus, the mist can be detected with the method described above.

The level of variation is detected as follows for example. First of all, whether or not the direction determination result is different from that in the previous frame is determined for each evaluation block (temporal variation level determination). Then, the direction determination result in the current frame of the evaluation block, with the direction determination result changed from that in the previous frame, is compared with those in peripheral evaluation blocks. The number of evaluation blocks with the different direction determination result is counted (spatial variation level determination). A block the total number of counted blocks of which has exceeded a threshold is determined to be a mist block. Thus, the mist block is an evaluation block that is determined to have a large temporal variation level and a large spatial variation level.

When the number of mist blocks exceeds a given threshold, the invalid frame setting section 2070 determines that the mist is detected and sets the current frame to be the invalid frame.

The invalid frame setting section 2070 may use a motion vector to perform the mist detection. For example, a motion vector representing the movement between two different images acquired at different timings (specifically, images in two frames in series) is obtained from the images. This motion vector is obtained for each of a plurality of points (regions) set on the image. Thus, a plurality of motion vectors are calculated from a process using the images in the two frames in series. The motion vector is susceptible to the mist, and thus, a special variation is large among the plurality of motion vectors obtained when the mist is produced.

Thus, the invalid frame setting section 2070 determines the reliability of the motion vector based on a spatial similarity among the motion vectors, to perform the mist detection. The motion vectors with a high spatial similarity are calculated based on a signal component and are not calculated based on a noise component, and thus are determined to be "reliable".

Specifically, first of all, one motion vector (hereinafter, referred to as a target motion vector) is selected from a plurality of local motion vectors in the image. Then, whether or not a motion vector adjacent to the target motion vector thus selected is a similar vector is determined, based on a difference between the target motion vector and the adjacent motion vector. This determination process is performed on all of the adjacent motion vectors. Then, the number of similar vectors is counted to be compared with a given threshold. The target motion vector with the number of similar vectors exceeding the threshold has spatial similarity with the peripheral motion vectors, and thus is determined to be "reliable". The target motion vector with the number of similar vectors not exceeding the threshold is determined to be "unreliable". This determination is performed on all of the motion vectors in the image, whereby whether or not each of the motion vectors is reliable is determined.

The reliability of the entire image is determined based on the reliabilities of the motion vectors, and the mist is determined to be detected for the image with a low reliability. For example, the mist may be determined to have been detected when the number or ratio of the motion vectors with low reliability exceeds a given threshold.

The invalid frame setting section 2070 may perform the mist detection by using both the direction determination result and the motion vectors. For example, the mist may finally be determined to have been detected, when the mist is detected with both of the direction determination result and the motion vectors. Thus, the mist detection can be performed with a higher accuracy.

The invalid frame setting section 2070 may set a target frame to be the invalid frame when an invalid subject is detected. Specifically, the invalid subject detection is performed based on the block state output from the block state determination section 2060. When the AF region is largely occupied by the invalid blocks (the treatment tool, a bright spot, a high luminance portion, a dark portion, and a block with the block AF evaluation value change rate β outside the given range), the focusing operation cannot be accurately performed. Thus, when the number of invalid blocks set in S205 exceeds a given threshold, it is determined that there is an invalid subject, and the target frame is set to be the invalid frame.

A scene resulting in the invalid frame set should not be maintained for a long period of time during an endoscopic procedure. Thus, the impact of the interruption of the focusing operation on the treatment by the user is limited.

As described above, the focus control section 2000 (processor) according to the present embodiment further includes the invalid frame setting section 2070 that sets the invalid frame based on at least one of the direction determination result for each of a plurality of regions and a feature amount of the plurality of pixels in the regions. The focus control section 2000 does not move the in-focus object plane position based on the direction determination result in the frame determined to be the invalid frame.

With this configuration, the in-focus object plane position can be prevented from being shifted in an inappropriate direction when the direction determination result is unreliable. The "movement based on the direction determination result" represents the movement of the focus lens by an amount corresponding to the shift amount of the wobbling center position. Still, even when the frame is set to be the invalid frame, the wobbling operation (the movement of the focus lens by the wobbling amount from the wobbling center position) for determining the direction cannot be prevented.

Thus, the invalid frame setting section 2070 (processor) sets the invalid frame based on at least one of the information on the spatial variation (variation level) of the direction determination result, information on the temporal variation of the direction determination result, and information on the variation of the motion vector serving as a feature amount.

The information on the temporal variation represents the level of variation (level of change) of the direction determination result in a given region over time as described above. The information on the spatial variation represents a level of variation between the direction determination result in a given region and the direction determination result in its periphery (four blocks on the upper, lower, left and right sides, eight surrounding blocks, or the like in the example of the evaluation blocks in FIG. 7 for example). The information on variation of the motion vector represents the level of variation among the plurality of motion vectors set on a single image.

With this configuration, the in-focus direction determination process or the like can be skipped when the mist is produced or when an image of an invalid subject is captured. Thus, a risk of moving the focus lens in a wrong direction can be reduced. Any one of the three types of variation information or a combination of any two of the three types of variation information may be used. When one of these types of information is used, the accuracy of the invalid frame determination might be compromised. For example, the block AF evaluation value change rate β is small around the in-focus position, resulting in a large temporal and spatial variation level. Thus, a frame might be erroneously determined to be the invalid frame, even when the invalid frame needs not to be set. The level of variation among motion vectors is small also around the in-focus position. Thus, the invalid frame can be accurately set by combining the variation information on the direction determination result with the variation information on the motion vector.

<Low Contrast State Determination>

The low contrast state determination section 2075 determines whether or not the subject is in the low contrast state based on the block AF evaluation value of each evaluation block output from the AF evaluation value calculation section 2030 and the invalid block setting result output from the invalid block setting section 2050 (S208).

Figure 12:
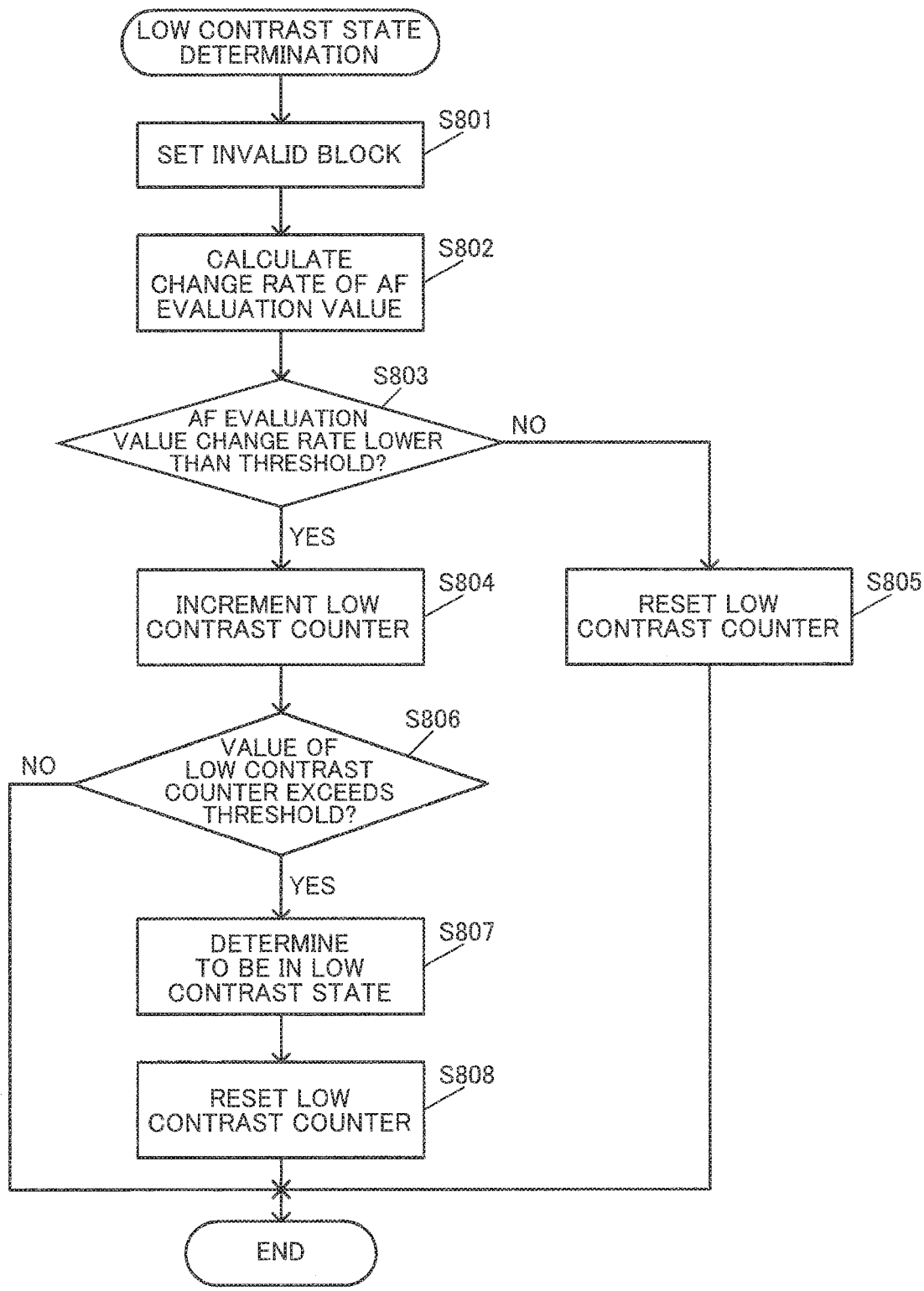
FIG. 12 is a flowchart illustrating a low contrast state determination process.

FIG. 12 is a flowchart illustrating a process performed by the low contrast state determination section 2075. When this process starts, first of all, the low contrast state determination section 2075 sets the invalid block (S801). Specifically, the low contrast state determination section 2075 acquires a result based on the block feature amount of an evaluation block from results of the process performed by the invalid block setting section 2050. Then, a block corresponding to a treatment tool, a bright spot, a high luminance portion, and a dark portion is set to be an invalid block (also referred to as a low contrast determination invalid block to be distinguished from the invalid block for the in-focus direction determination) not used in the low contrast state determination. Note that this should not be construed in a limiting sense, and only a block corresponding to any desired subject may be set to be the low contrast invalid block.

The low contrast state determination section 2075 sets a block, in the plurality of evaluation blocks, other than the low contrast determination invalid block, to be a valid block (low contrast determination valid block), and calculates the change rate of the AF evaluation values from the AF evaluation values in the valid blocks (S802). Specifically, the low contrast state determination section 2075 calculates an average value AreaAfVal[N] of the AF evaluation values of all of the valid blocks. The average value corresponds to the AF evaluation value of the entire AF region excluding the treatment tool, the bright spot, the high luminance portion, and the dark portion.

An AF evaluation value change amount α' and an AF evaluation value change rate β' are respectively calculated with the following Formulae (6) and (7), where AreaAfVal[N−1] and AreaAfVal[N−2] respectively represent the average values of the AF evaluation values similarly calculated in the previous frame and the frame immediately before the previous frame. Specifically, the information obtained in S802 is the AF evaluation value change rate β'.

$$\alpha' = \{(\text{AreaAfVal}[N] + \text{AreaAfVal}[N-2])/2\} - \text{AreaAfVal}[N-1] \qquad (6)$$

$$\beta' = |\alpha'|/\text{Ave}(\text{AreaAfVal}[N], \text{AreaAfVal}[N-1], \text{AreaAfVal}[N-2]) \qquad (7)$$

Note that Formula (6) described above is similar to Formula (3) described above. Only difference is that the AF evaluation value used in Formula (3) described above is the block AF evaluation value AfVal in each block, and the AF evaluation value in Formula (6) described above is the average value AreaAfVal of the AF evaluation values of all of the low contrast determination valid blocks. With Formula (6) described above, the change amount of the AF evaluation value can be stably obtained as in the example using Formula (3) described above.

Formula (7) described above is similar to Formulae (4) and (5) described above, and the AF evaluation value change rate β' is a value obtained by normalizing the AF evaluation value change amount α'. With this configuration, an impact of the contrast of the brightness of the subject can be reduced. Whether the direction determination process is a positive value or a negative value needs not be determined in the low contrast state determination. Thus, the absolute value of the AF evaluation value change amount α' is used in Formula (7) described above.

The low contrast state determination section 2075 determines whether or not the AF evaluation value change rate β' is equal to or lower than a given threshold (S803). When the AF evaluation value change rate β' is equal to or lower than the threshold (Yes in S803), the current frame is determined to be the low contrast frame, and the value of the low contrast counter is incremented (S804). When the current frame is not in the low contrast frame (No in S803), the value of the low contrast counter is reset (set to be 0) (S805). Note that the value of the low contrast counter may be decremented in S805. In a configuration where the value is decremented, the value of the low contrast counter may be limited so as not to be equal to or lower than 0.

The low contrast state determination section 2075 determines whether or not the value of the low contrast counter exceeds a threshold (S806), and determines that the subject is in the low contrast state when the threshold is exceeded (S807). When the subject is determined to be in the low contrast state, the value of the low contrast counter is reset (S808).

As described above, the low contrast state determination section 2075 (processor) determines that the target subject is in the low contrast state, when a variation of the AF evaluation value of a region, in a plurality of regions, other than the invalid region (low contrast determination invalid block) is smaller than a given threshold. Specifically, the low contrast state determination section 2075 determines that the target subject is in the low contrast state when the variation of the AF evaluation value as a result of moving the in-focus object plane position in the direction determination process is smaller than a given threshold.

The AF evaluation value of the region other than the invalid region corresponds to AreaAfVal in Formulae (6) and (7) described above, the variation of the AF evaluation value corresponds to β' (and α') described above. With this method, the low contrast state can be accurately determined for an image including a treatment tool with a high contrast, a bright spot, and the like.

The focus control section 2000 performs determination based on a result of S208 (S209). When the subject is determined to be in the low contrast state (Yes in S209), the focus lens position is determined (S213) with the processes in S210 to S212 skipped.

When the subject is determined not to be in the low contrast state (No in S209), the focus control section 2000 determines whether or not the target frame has been set to be the invalid frame by the invalid frame setting section 2070 (S210). When the target frame has been set to be the invalid frame, the focus lens position is determined (S213) with the processes such as the in-focus direction determination process (S211) and the in-focus determination (S212) skipped. The processes in S211 to S213 are sequentially performed when the target frame is not set to be the invalid frame.

<In-Focus Direction Determination>

The in-focus direction determination section 2080 determines the final in-focus direction, based on the block state of each evaluation block output from the block state determination section 2060 in S206 (S211).

As described above, the focus control section 2000 according to the present embodiment includes the invalid region setting section (invalid block setting section 2050) that sets the invalid region, based on the AF evaluation value of each of the plurality of regions or a feature amount of the plurality of pixels in the regions. Thus, the focus control section 2000 (in-focus direction determination section 2080) determines that the in-focus direction is toward the NEAR side, when a ratio (nearRatio) of NEAR area information to area information on valid regions that are a plurality of regions excluding at least the invalid region is larger than a given threshold (TH_NEAR) corresponding to the weight information.

Figure 13:
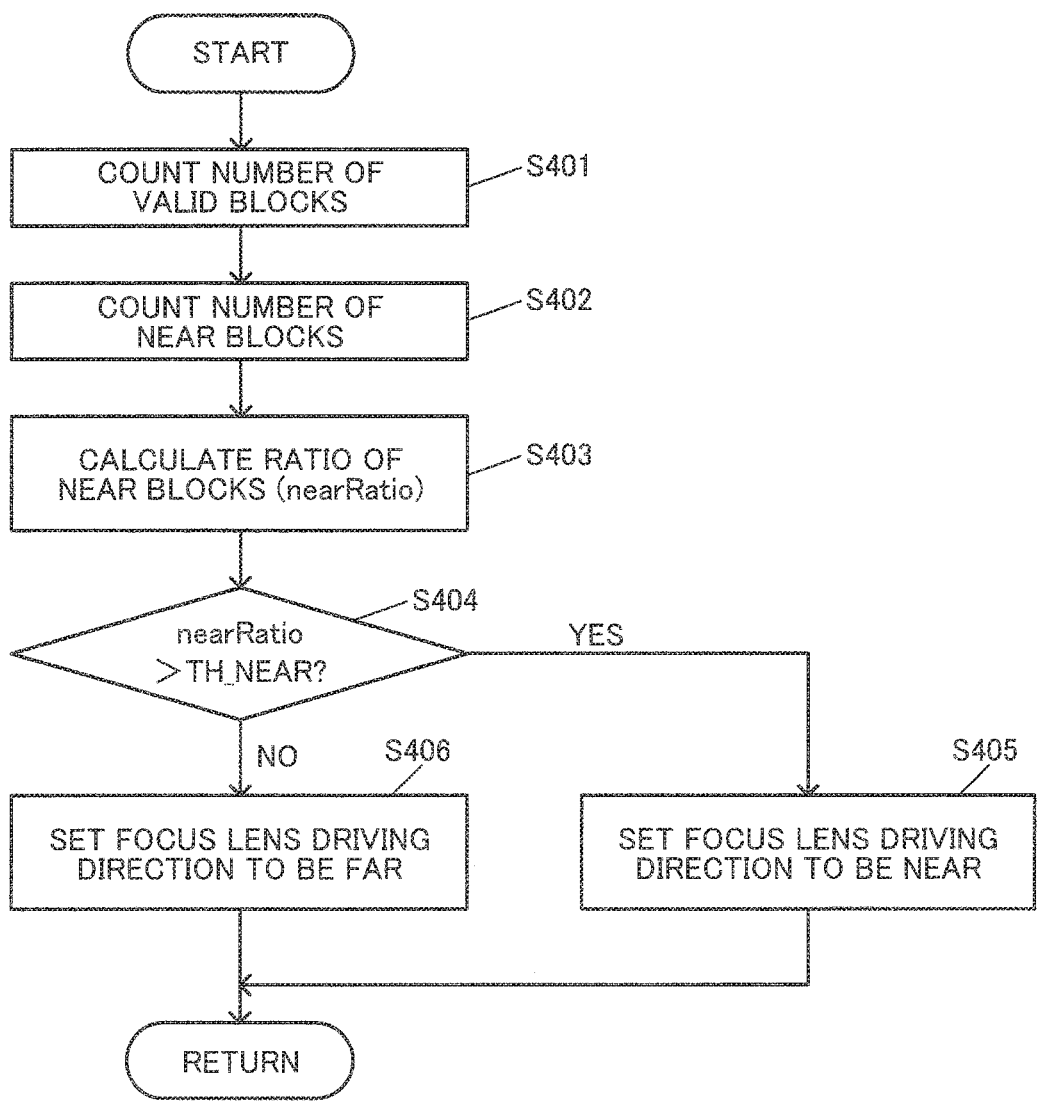
FIG. 13 is a flowchart illustrating an in-focus direction determination process.

FIG. 13 is a flowchart illustrating a process performed by the in-focus direction determination section 2080. When this process starts, first of all, the number of valid blocks in the AF region is counted (S401). The valid block is an evaluation block that is not the invalid block. When the block state includes three states of NEAR, FAR, and invalid, the number of valid blocks is the sum of the numbers of the NEAR blocks and the FAR blocks.

Next, the number of blocks with the block state NEAR is counted (S402), the ratio (nearRatio) of the NEAR blocks to the valid blocks is calculated (S403). Then, whether or not the nearRatio exceeds the threshold TH_NEAR (S404), and the in-focus direction is determined based on a result of this determination. This corresponds to a process of determining the in-focus direction through the weighted comparison between the NEAR blocks and the FAR blocks described above.

Specifically, the in-focus direction is determined to be NEAR when nearRatio >TH_NEAR is satisfied (S405) and is determined to be FAR when nearRatio ≤TH_NEAR is satisfied (S406).

With this process, for example, the tissue can be accurately brought into focus even when a part of the treatment tool is failed to be detected as the invalid block and thus is detected as the valid block in the invalid block setting process in S205. This is because even when a part of the treatment tool is set to be the valid block to have the block state (direction) different from the block state (direction) of the tissue, the in-focus direction is determined with the blocks state of the tissue because the number of the block corresponding to the tissue is larger in the AF region as a whole.

Figure 14:
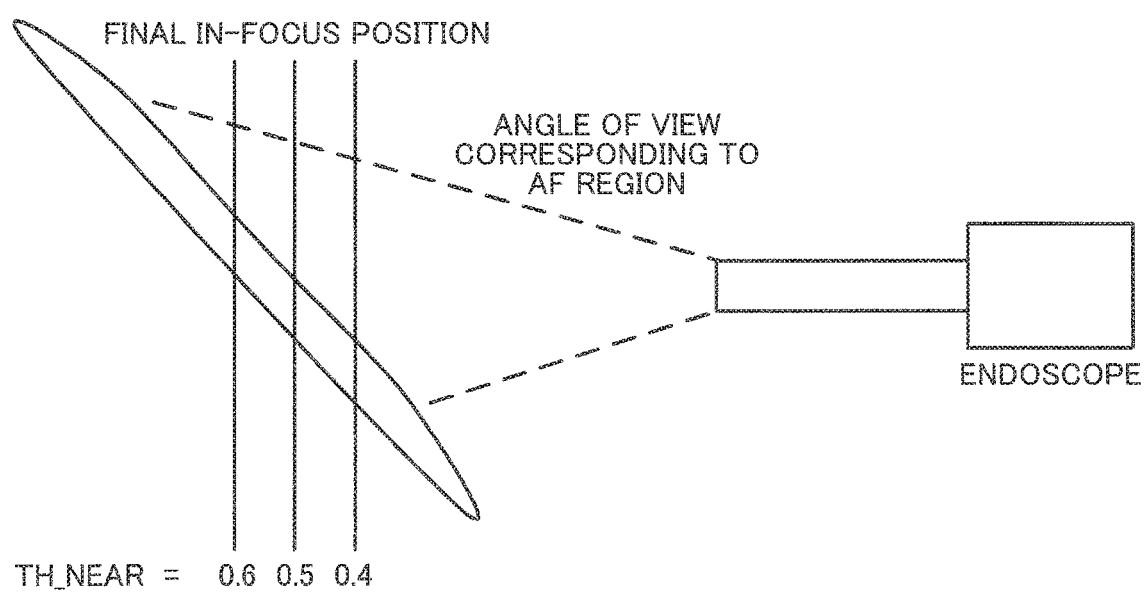
FIG. 14 illustrates an example of how an in-focus position is adjusted by adjusting second weight information (threshold).

When the subject has a depth as illustrated in FIG. 14, in the process, a larger value of TH_NEAR leads to the final in-focus position set to be more on the deep side (farther from the imaging section 200). This is because when the value of TH_NEAR is large, the in-focus direction is not determined to be NEAR and the in-focus object plane position is moved toward the FAR side unless the ratio of the NEAR block is considerably high.

Thus, for example, the user can adjust the in-focus position as desired by adjusting the value of TH_NEAR.

Alternatively, the focus control section 2000 according to the present embodiment further includes a target distance estimation section (not illustrated in FIG. 4 and the like) that estimates a relative distance between the subject determined to be the target of the user and the imaging section 200, based on the image. Thus, the focus control section 2000 may change the threshold based on a result of the estimation by the target distance estimation section. For example, the focus control section 2000 (in-focus direction determination section 2080) may automatically adjust the value of TH_NEAR based on a result of estimation of the state of the subject from a luminance distribution of the entire image by the target distance estimation section.

Figure 15:
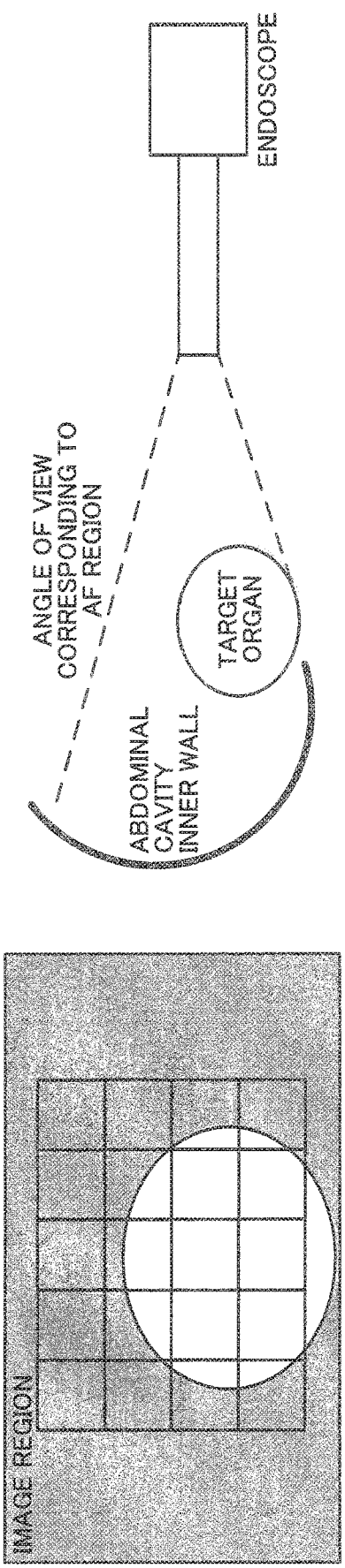
FIG. 15 is a diagram illustrating a target distance estimation process.

Specifically, the target of the user can be estimated to be an organ position on a closer side in an abdominal cavity when an image with a bright center portion and a dark peripheral portion as illustrated in FIG. 15 is used. In such a case, the target organ positioned on the closer side can be accurately brought into focus, with the value of TH_NEAR set to be small.

Thus, the focus control section 2000 according to the present embodiment performs comparison between the NEAR area information and the FAR area information that have been weighted by the second weight information, as the weighted comparison. With this configuration, the in-focus position (the in-focus object plane position with the target subject determined to be in focus, or the focus lens position achieving the in-focus object plane position) can be flexibly set.

The method according to the present embodiment described above uses the second weight information. Note that the first weight information may also be used in the present embodiment.

The focus control section 2000 according to the present embodiment further includes the target region estimation section (not illustrated in FIG. 4 and the like) that estimates a region determined to be a target of the user, based on image. The focus control section 2000 may set weight information (first weight information) achieving a large weight on the region estimated by the target region estimation section, and may calculate the NEAR area information based on the weight information set.

Figure 16:
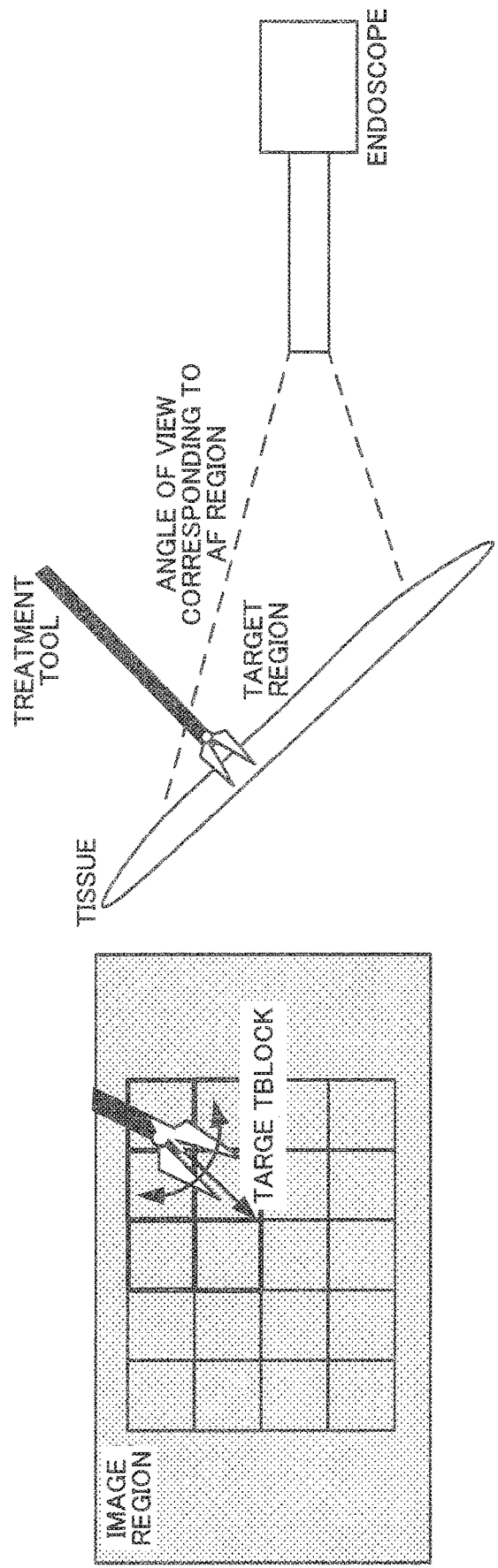
FIG. 16 is a diagram illustrating a target region detection process.

For example, when the user performs a treatment on a target as a part of a subject with a depth as illustrated in FIG. 16, the target region of the user needs to be accurately brought into focus. In this case, for example, the target region estimation section first estimates the target block corresponding to the target region as illustrated in FIG. 16, and the focus control section 2000 (in-focus direction determination section 2080) counts the weight N (the first weight information, N>1) of the target block. With this process, the weight on the state (direction) of the target block increases in the calculation of the nearRatio. As a result, the weight of the state of the target block for determining the in-focus direction also increases, whereby the target region can be accurately brought into focus.

Thus, the focus control section 2000 according to the present embodiment obtains the NEAR area information based on the first weight information set to the region determined to be NEAR. As described above, when all of the plurality of regions (evaluation blocks) have the same area, the sum of the weights of the regions determined to be NEAR serves as the NEAR area information. The NEAR area information can be more generalized, that is, may be the sum of the products of the areas and the weight information of the regions. With this configuration, the target region in the image can be appropriately brought into focus.

The target block may be estimated as follows for example. The region where the user performs the treatment involves a large variation of the treatment tool and the tissue. Thus, the AF evaluation value and the block feature amount (color information, luminance information) of the evaluation block largely changed within a short period of time. Thus, the target block may be estimated from an amount of change of these values over time. A motion vector of the evaluation block may be calculated by using a known method, and the target block may be estimated based on the amount of change in the magnitude and the direction of the motion vector over time. The block with a large amount of change as well as its peripheral blocks may be estimated to be the target block so that a ratio of the invalid block (treatment tool) in the target block can be prevented from being large.

Figure 17:
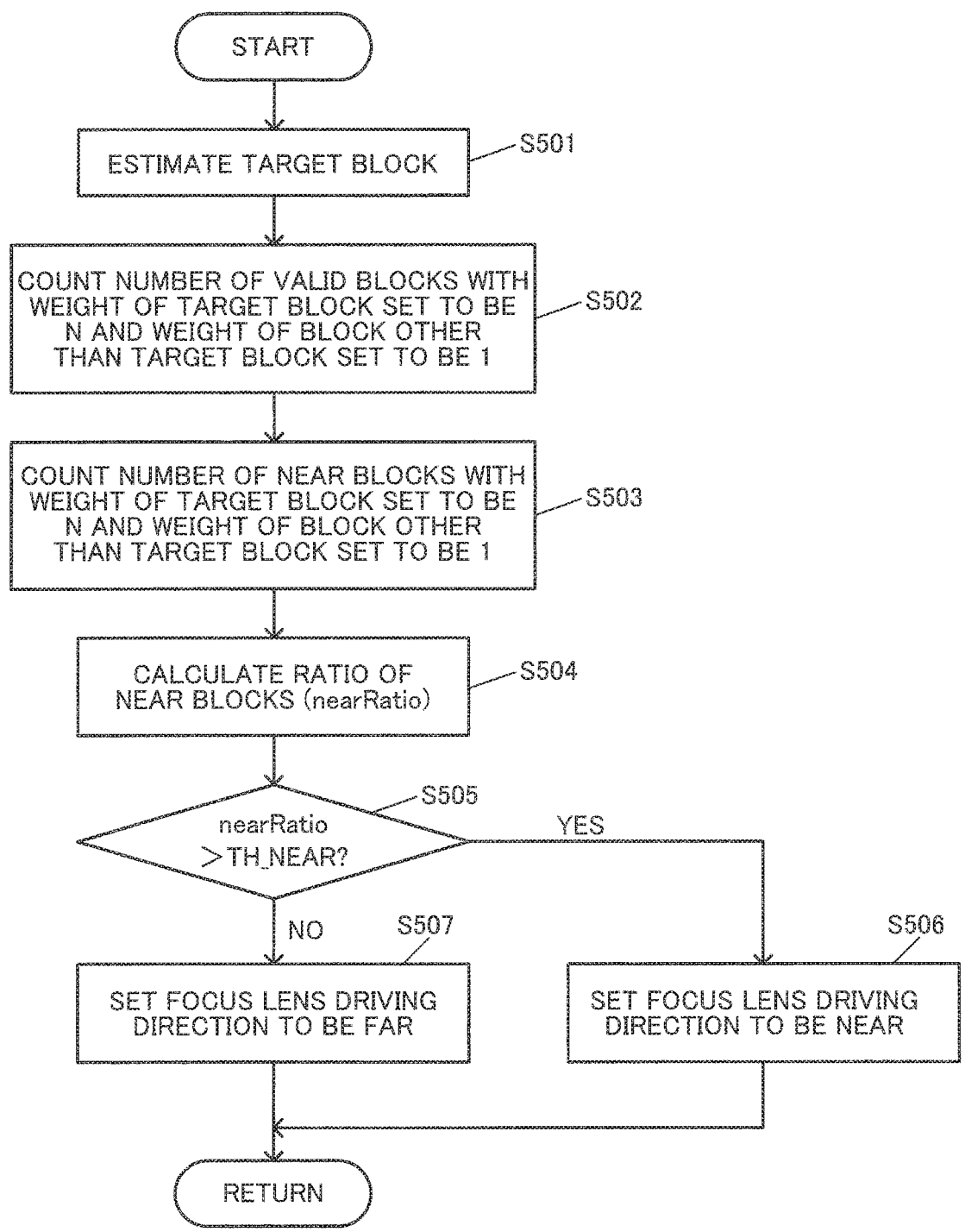
FIG. 17 is another flowchart illustrating the in-focus direction determination process.

FIG. 17 is a flowchart illustrating a process using the first weight information. When this process starts, first of all, the target block is estimated (S501). Then, the valid blocks are counted (S502). Note that S502 is different from S401 in that the weight N is used for the counting. Specifically, the blocks are counted with the weight of the target block being N and the weight of a block other than the target block being 1. The number of NEAR blocks are counted in a similar manner, that is, counted with the weight of the target block being N and the weight of a block other than the target block being 1 (S503).

The processes in S504 to S507, after the counting, are respectively the same as those in S403 to S406 in FIG. 13.

<In-Focus Determination>

The in-focus determination section 2090 determines whether or not the focus lens has reached the in-focus position based on the in-focus direction (NEAR/FAR) output from the in-focus direction determination section 2080 and a position where the in-focus direction has been reversed (S212).

Figure 18:
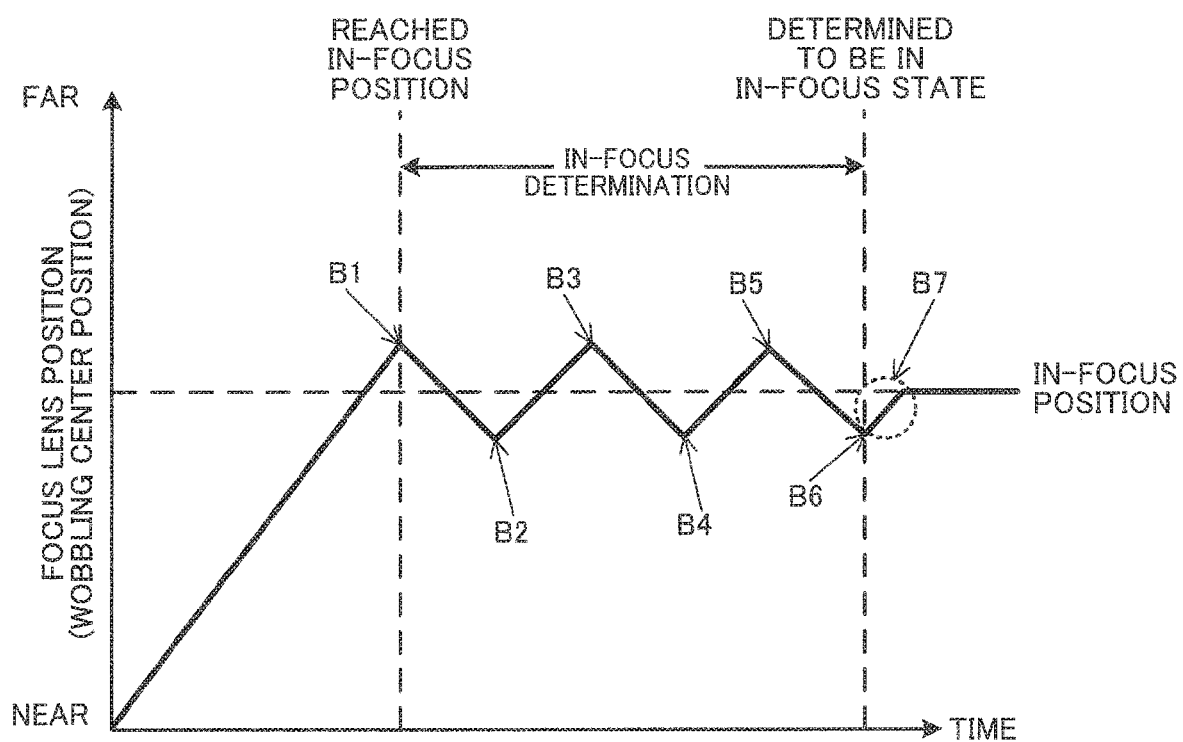
FIG. 18 is a diagram illustrating how the focus lens is controlled in an in-focus determination process.

The focus lens that has reached the in-focus position makes a reciprocating motion relative to the in-focus position as illustrated in FIG. 18. This is because the in-focus direction is not reversed unless that lens passes through the in-focus position by a certain distance due to an extremely small value of the block AF evaluation value change rate β at the in-focus position. In the in-focus state, the in-focus direction is always reversed at substantially the same position. Thus, whether or not the in-focus state is achieved can be determined by determining whether or not the following two conditions are satisfied: (1) the reciprocating motion is performed for a given number of times; and (2) the variation of the reversing position of the reciprocating motion is small.

Figure 19:
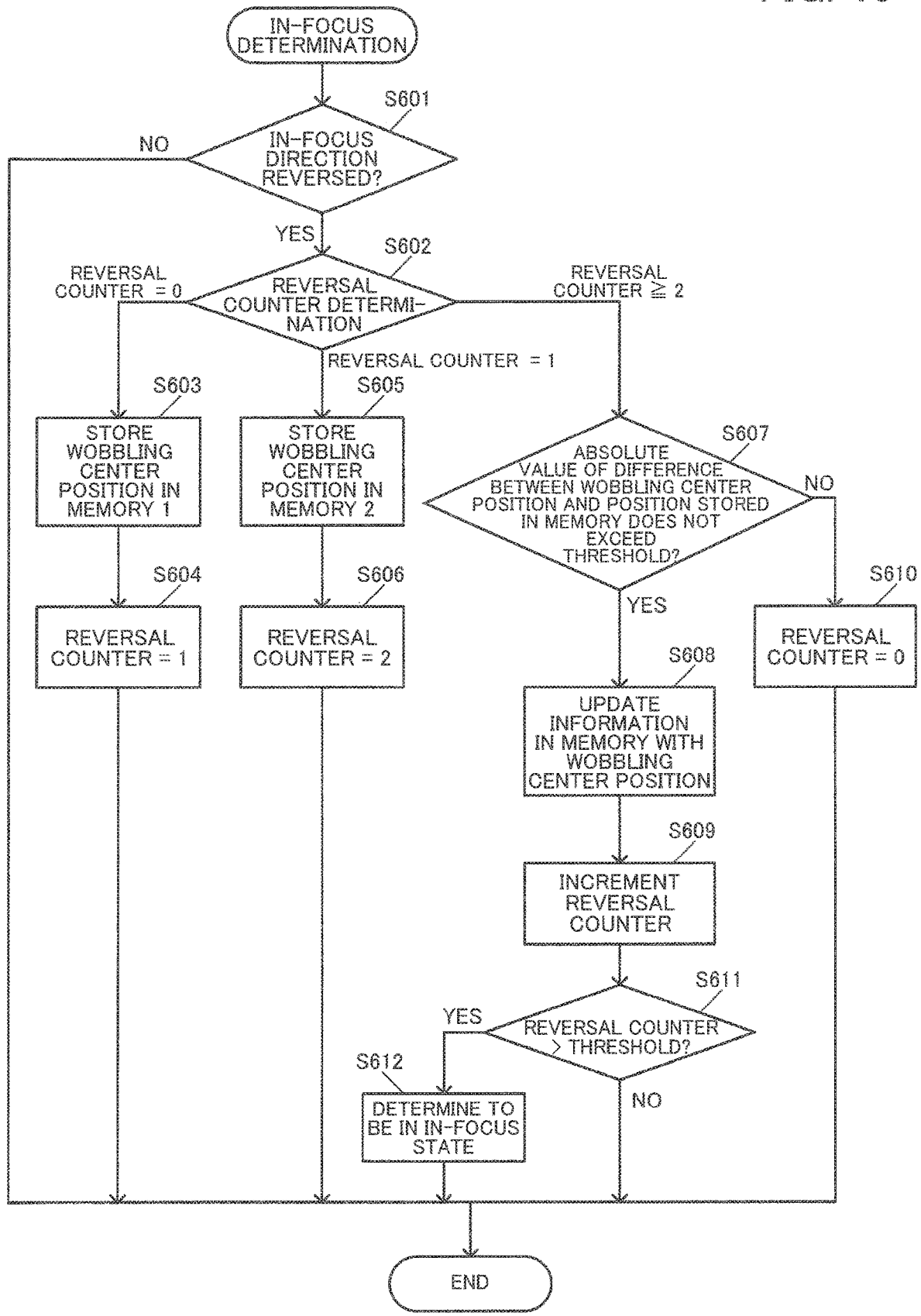
FIG. 19 is a flowchart illustrating the in-focus determination process.

FIG. 19 is a flowchart illustrating a process performed by the in-focus determination section 2090. When this in-focus determination process starts, first of all, whether or not the in-focus direction has been reversed is determined (S601). When a result of the determination in S601 is No, the in-focus determination process in the current frame is terminated.

When a result of the determination in S601 is Yes, a value of the reversal counter is determined (S602). The reversal counter is a counter indicating the number of times the in-focus direction has been reversed. When the value of the reversal counter is 0, the wobbling center position at the time when the in-focus direction is reversed is stored in the memory 1 (S603), and the reversal counter is incremented (S604) to be 1 at this timing. In FIG. 18, the focus lens position (wobbling center position) at B1 is stored in the memory 1.

When the value of the reversal counter is 1, the wobbling center position at the time when the in-focus direction is reversed is stored in the memory 2 (S605), and the reversal counter is incremented (S606) to be 2 at this timing. In FIG. 18, the focus lens position (wobbling center position) at B2 is stored in the memory 2.

Through the processes in S603 and S605, reference positions on the FAR side and the NEAR side in the reciprocating motion are stored in the memories. Whether the memory 1 corresponds to NEAR or FAR depends on the situation. In the reversal detection thereafter, whether or not the variation between the wobbling center position at the time of the detection and the reference position stored in the memory is small may be determined.

Specifically, in S602, when the value of the counter is 2 or more, the wobbling center position at the time when the in-focus direction is reversed is compared with the position (the value stored in the memory 1 or the memory 2) at the time when the in-focus direction is reversed by the reversing immediately before the previous reversing, and whether or not a resultant difference (absolute value) is equal to or smaller than a threshold is determined (S607). The position at the time when the in-focus direction is reversed by the reversing immediately before the previous reversing is used as a comparison target because the reversing from FAR to NEAR and reversing from NEAR to FAR are alternately detected as illustrated in FIG. 18. For example, information obtained at B3 is compared with the information obtained at B1, that is, the information in the memory 1, and information obtained at B4 is compared with the information obtained at B2, that is, the information in the memory 2.

When the resultant difference is equal to or small than the threshold (Yes in S607), the information, in the memory 1 or the memory 2, used in the comparison is updated with the wobbling center position in the current frame (S608), and the reversal counter is incremented (S609). At the timing B3, the information in the memory 1 is updated with the wobbling center position at this timing, and at the timing B4, the information in the memory 2 is updated with the wobbling center position at this timing. The same applies to the subsequent timings. When the difference is larger than the threshold (No in S607), the in-focus state is determined to be not achieved and the counter is set to 0 (S610).

After the process in S609, whether or not the reversal counter has exceeded a focusing completion determination threshold is determined (S611). When a result of the determination in S611 is Yes, the in-focus state is determined to be achieved (S612). In the example illustrated in FIG. 18, the reversal counter >5 is set as the condition, and thus the result of the determination in S612 is Yes at the timing B6 at which the reversing occurs for the sixth time.

As described above, the focus control section 2000 (corresponding to the processor and the in-focus determination section 2090) stops the focusing operation when the count (reversal counter) indicating how many times switching of the movement of the in-focus object plane position from the NEAR to the FAR or from the FAR to the NEAR has occurred exceeds a given switching threshold (the focusing completion determination threshold). This corresponds to the determination in S611 described above. In this process, the focus control section 2000 resets the count indicating how many times the switching has occurred, when a variation of the in-focus object plane position corresponding to switching from the NEAR to the FAR or a variation of the in-focus object plane position corresponding to switching from the FAR to the NEAR exceeds a given variation threshold. This corresponds to the processes in S607 and S610 described above. The relationship between the in-focus object plane position and the focus lens position is likely to be recognized when the focus control device (endoscope apparatus) is designed. Thus, the in-focus object plane position can also be regarded as the focus lens position.

With this configuration, the in-focus determination can be performed based on whether or not the reciprocating motion illustrated in FIG. 18 has occurred.

<Focus Lens Position Determination>

The focus lens position determination section 2095 determines the next focus lens position by using the determination result obtained by the low contrast state determination section 2075, the setting result obtained by the invalid frame setting section 2070, the in-focus direction determined by the in-focus direction determination section 2080, and the determination result obtained by the in-focus determination section 2090 (S213).

Figure 20:
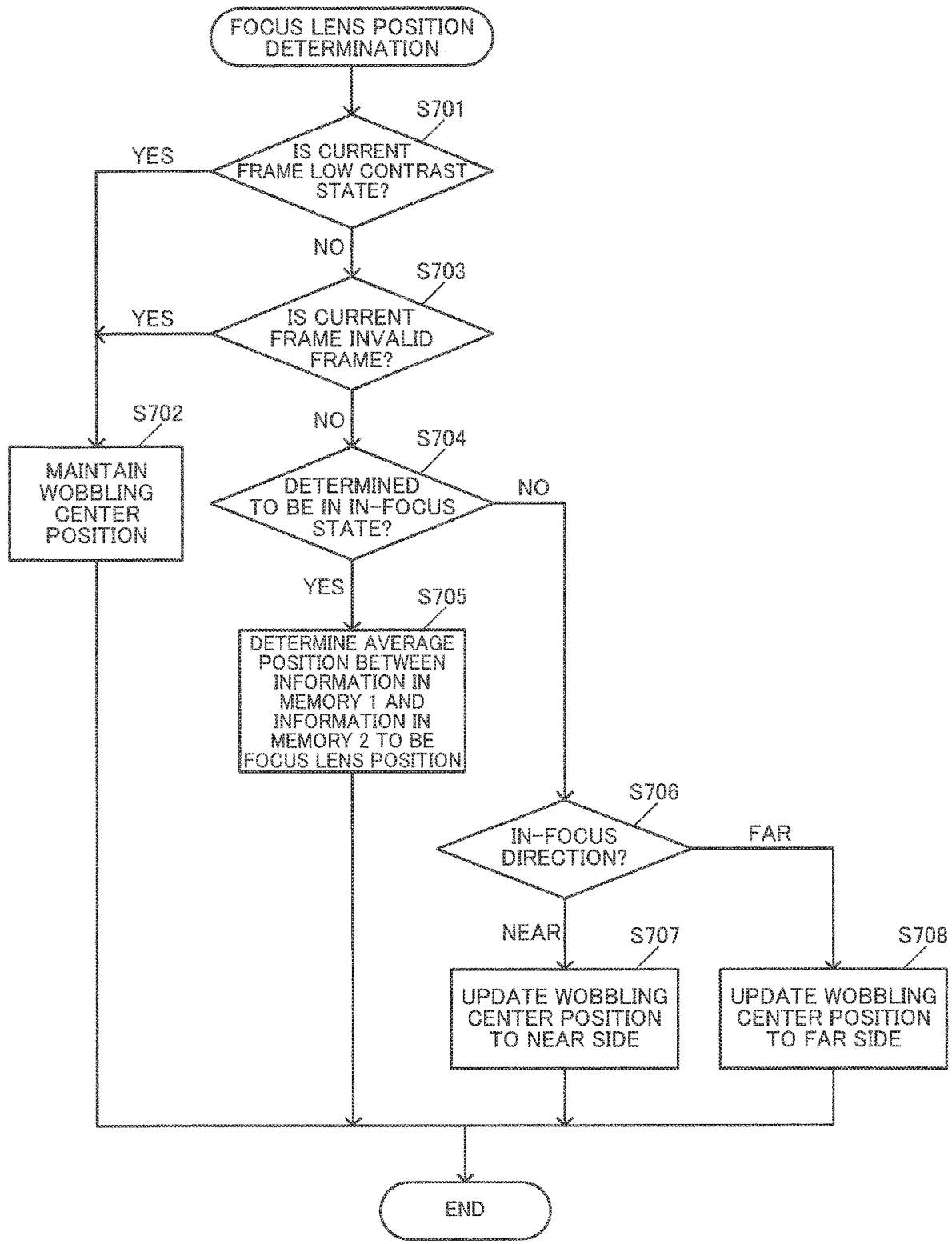
FIG. 20 is a flowchart illustrating a focus lens position determination process.

FIG. 20 is a flowchart illustrating a process performed by the focus lens position determination section 2095. When this process starts, first of all, whether or not the subject is in the low contrast state is determined (S701). When the subject is determined to be in the low contrast state, the focus lens position is determined to maintain the current wobbling center position (S702). Specifically, the shift amount is set to be 0, and the current wobbling operation is maintained.

Then, whether or not the current frame is the invalid frame is determined (S703). When the current frame is the invalid frame (Yes in S703), the focus lens position is determined to maintain the current wobbling center position (S702).

When the result is No in both of S701 and S703, whether or not the subject has been determined to be in-focus in S212 is determined (S704). When the subject has been determined to be in-focus, the focus lens position is set to be the average position of the values stored in the memories 1 and 2 (S705). At the timing B6 when the subject is determined to be in-focus in FIG. 18, the wobbling center position at the timing B5 is stored in the memory 1 and the wobbling center position at the timing B6 is stored in the memory 2. Thus, the process in S705 corresponds to a process of determining the focus lens position implementing the focus lens movement for B7.

When the subject is determined to be out of focus, the in-focus direction determined in S211 is determined (S706). When the in-focus direction is NEAR, the focus lens position is determined so that the wobbling center position moves toward the NEAR side (so that the in-focus object plane position moves toward the imaging section 200) by the shift amount (S707). When the in-focus direction is FAR, the focus lens position is determined so that the wobbling center position moves toward the FAR side (so that the in-focus object plane position moves away from the imaging section 200) by the shift amount (S708).

With the process described above, an endoscope apparatus can be implemented that has an AF control function with which the tissue can be brought into focus with the low contrast state determination accurately performed even when a status of a treatment tool with a high contrast, a bright spot, and the like largely changes.

5. MODIFICATIONS

The method according to the present embodiment is not limited to that described above, and various modifications may be made. Modifications of the processes performed by the sections of the AF control section 340 are described below.

<Block AF Evaluation Value and Direction Determination>

The AF evaluation value calculation section 2030 is not limited to the calculation of a single block AF evaluation value for a single block, and may calculate a plurality of block AF evaluation values using a plurality of band pass filters with different frequency bands. The direction determination section 2040 may obtain the block AF evaluation value change rate $\beta$ from each of the plurality of block AF evaluation values, and may determine the block direction based on the block AF evaluation value change rate $\beta$. Thus, the block direction determination can be accurately performed for a subject with various frequency bands. For example, the direction determination section 2040 obtains the direction determination result from a plurality of block AF evaluation value change rates $\beta$, and may prioritize a result obtained from a frequency band that is expected to be a target of the user, when different results are obtained.

<Invalid Block Setting and Block State Determination>

The value (absolute value) of the block AF evaluation value change rate β is extremely small around the in-focus position. Thus, the block state of most of the blocks might be determined to be invalid, resulting in a failed focusing operation. To address this, a modified process may be performed with a block with the block AF evaluation value change rate β not exceeding a threshold (low contrast) not be set as the invalid block.

Specifically, the invalid block setting section 2050 sets an evaluation block with an excessively high block AF evaluation value change rate β, an evaluation block occupied by a treatment tool (silver color or block color), a bright spot, and the like, and an evaluation block corresponding to a high luminance portion, a dark portion, or the like to be the invalid block, and sets an evaluation block with an excessively low block AF evaluation value change rate β to be a low contrast block.

Figure 21:
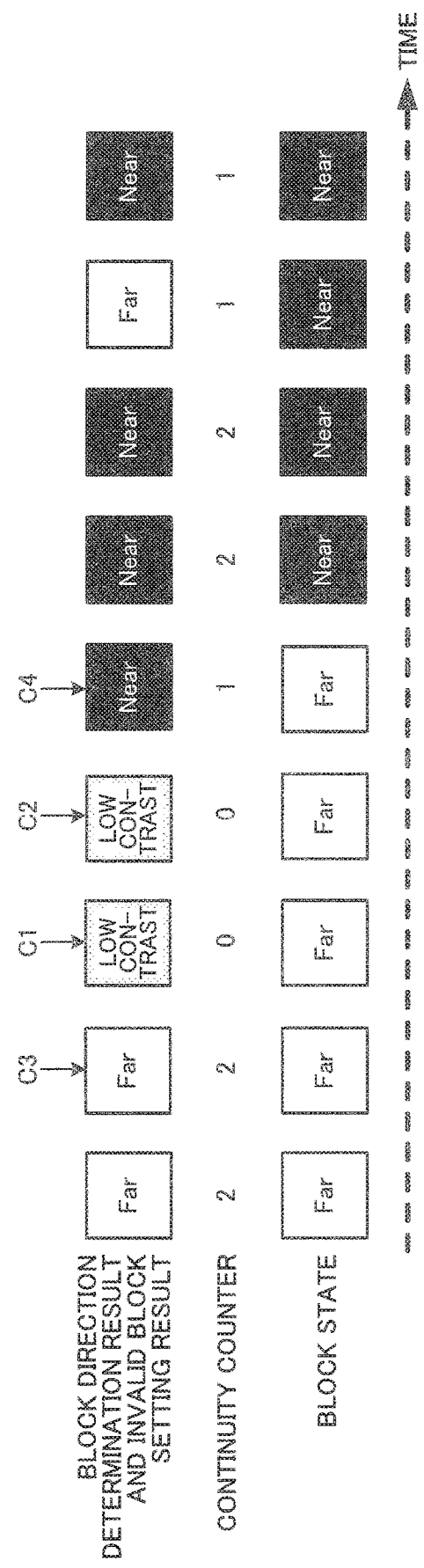
FIG. 21 illustrates a specific example of how the block state changes over time.

When the current frame is the low contrast block, the block state determination section 2060 maintains the block state of the previous frame, instead of setting the block state to be invalid. FIG. 21 illustrates a specific example where the subject is determined to be in the low contrast state and the continuity counter is reset to 0 in frames C1 and C2. Still, the block state in the previous frame is maintained in these frames (the block state FAR in a frame C3 in FIG. 21). In a portion around the in-focus position, the absolute value of the block AF evaluation value change rate β increases again when the focus lens passes through the in-focus position. Thus, the low contrast state does not continue for a long period of time. For example, a result other than the low contrast is acquired as in a frame C4 in FIG. 21, and the reciprocating motion around the in-focus position continues.

Thus, a state where the low contrast state continues for a long period of time can be determined to be different from a state where the block AF evaluation value change rate β temporarily decreases around the in-focus position. For example, this state corresponds to a state where a blurring level is too high (largely blurred state) and a state where the subject is in the low contrast state, in which the direction cannot be determined by the wobbling operation. Thus, the number of times the previous block state was maintained (or the number of times the low contrast state was maintained) is counted, and the subject may be determined to be in the low contrast subject and the block state may be set to be invalid when a result of the counting exceeds a threshold.

<Invalid Frame Setting>

In the example described above, the invalid frame setting section 2070 obtains a motion vector based on an image. However, this should not be construed in a limiting sense, and sensor information from a motion sensor may be used. The motion sensor is a sensor that detects a motion of the imaging section 200, such as an accelerometer or a gyro sensor.

In the above description, the invalid frame setting section 2070 employs a method based on the mist detection or the invalid subject detection. Note that the invalid frame may be set through other methods. Specifically, an accurate focusing operation is difficult to achieve due to motion blur while the imaging section 200 is moving. Thus, the invalid frame setting section 2070 performing the above described method may further detect the motion of the imaging section 200 and set a frame involving the motion of the imaging section 200 to be the invalid frame.

Specifically, when the magnitude of the motion vector is larger than a given threshold, the frame is set to be the invalid frame. For this motion vector, information that is similar to that of the motion vector used for the mist detection may be used. Note that a large motion vector corresponding to the treatment tool is obtained also when the treatment tool is largely moving with no relative movement between the imaging section 200 and the target subject (tissue). However, the motion blur is not large in such a situation, and thus the frame needs not to be the invalid frame. Thus, a local motion vector and a global motion vector may be obtained as the motion vectors, and the invalid frame may be set based on the global motion vector as one of the motion vectors.

<Low Contrast State Determination>

In the above description, the low contrast state determination section 2075 calculates the average value AreaAfVal of the AF evaluation values of the valid blocks (low contrast determination valid blocks) in the current frame, to determine whether or not the subject is in the low contrast state. However, this should not be construed in a limiting sense. Block AF evaluation values and low contrast determination invalid blocks in the current frame and two previous frames may be stored in the memory, and blocks determined to be the valid block in all of the current frame and the two previous frames may be finally set as the valid block.

Also in this configuration, Formulae (6) and (7) may be used for calculating the AF evaluation value change amount α' and the AF evaluation value change rate β'.

<In-Focus Direction Determination>

In the above description, the in-focus direction determination section 2080 determines the in-focus direction based on the block state in the current frame. However, this should not be construed in a limiting sense. The in-focus direction determination section 2080 may perform a process of updating the in-focus direction when the same in-focus direction is maintained for a plurality of times. With such a process, the stable focusing operation can be implemented with the in-focus direction prevented from frequently changing.

<In-Focus Determination>

The condition used by the in-focus determination section 2090, including the small variation (change) in each of the position where the reversal from FAR to NEAR occurs and the position where the reversal from NEAR to FAR occurs, may further include other conditions. For example, a variation of the width of the reciprocating motion relative to the in-focus position is obviously not large. Thus, an excessively large or small difference between the position of the previous reversing and the position of the latest reversing results in a low reliability. Thus, the in-focus state can be determined to be not achieved when a distance (difference, absolute value of the difference) between the position where the reversing from FAR to NEAR has occurred and the position where the reversing from NEAR to FAR has occurred is outside a given range.

<Focus Lens Position Determination>

The shift amount for moving the wobbling center position to the in-focus direction may be a given fixed value, or may be gradually increased when the same direction determination result is maintained. With such a process, a time required for the focus lens to reach the in-focus position can be shortened (high speed focusing operation can be achieved).

The shift amount may be reduced when the focus lens reaches the in-focus position and starts the reciprocating motion. With such a process, a small amplitude of the reciprocating motion can be achieved, whereby deterioration of the image quality due to the reciprocating motion during the in-focus determination can be reduced. The amplitude of the reciprocating motion corresponds to the difference between the position of the reversing from FAR to NEAR and the position of the reversing from NEAR to FAR described above in the modification of the in-focus determination section 2090. Thus, when the in-focus determination section 2090 determines whether or not the amplitude of the reciprocating motion is within a given range, the "given range" is preferably set while taking the shift amount into consideration.

Although only some embodiments of the present invention and the modifications thereof have been described in detail above, those skilled in the art will readily appreciate that many modifications are possible in the embodiments without materially departing from the novel teachings and advantages of the invention. Accordingly, all such modifications are intended to be included within the scope of the invention. For example, any term cited with a different term having a broader meaning or the same meaning at least once in the specification and the drawings can be replaced by the different term in any place in the specification and the drawings. The configurations and the operations of the focus control device and the endoscope apparatus are not limited to those described above in connection with the embodiments. Various modifications and variations may be made of those described above in connection with the embodiments.

What is claimed is:

1. A focus control device comprising:
a processor comprising hardware, wherein the processor is configured to:
   set a plurality of regions, each including a plurality of pixels, in an image acquired by an image sensor;
   calculate an autofocus (AF) evaluation value of each of the plurality of regions set;
   set a region, in the plurality of regions, determined to include a subject other than a target subject to be an invalid region;
   determine whether or not the target subject is in a low contrast state based on the AF evaluation value of a region, in the plurality of regions, other than the invalid region; and
   control an in-focus object plane position based on the AF evaluation value,
   wherein the processor is configured to:
      perform a first control of the in-focus object plane position in response to determining that the target subject in the plurality of regions, other than the invalid region, is not in the low contrast state; and
      perform a second control, different from the first control, of the in-focus object plane position in response to determining that the target subject in the plurality of regions, other than the invalid region, is in the low contrast state,
      wherein, in performing the second control, the processor is configured to perform a reset operation of moving a focus lens to a given position and control the in-focus object plane position after the reset operation is performed.

2. The focus control device according to claim 1, wherein the processor is configured to:
   determine whether a variation of the AF evaluation value of the region, in the plurality of regions, other than the invalid region is smaller than a given threshold; and
   determine that the target subject is in the low contrast state in response to determining that the variation of the AF evaluation value of the region, in the plurality of regions, other than the invalid region is smaller than the given threshold.

3. The focus control device according to claim 2, wherein the processor is configured to:
   obtain a direction determination result for each region in some or all of the plurality of regions, by determining whether a target focusing position that is a target of the in-focus object plane position is on a near side or a far side relative to a reference position;
   determine an in-focus direction based on the direction determination result;
   control the in-focus object plane position based on the in-focus direction; and
   determine that the target subject is in the low contrast state when the variation of the AF evaluation value as a result of moving the in-focus object plane position is smaller than the given threshold.

4. The focus control device according to claim 1, wherein the processor is configured to, after the reset operation is performed, prevent the reset operation from being performed for a given period of time.

5. The focus control device according to claim 1, wherein the processor is configured to:
   count a number of reset times indicating a number of times the reset operation has been performed; and
   but the control on the in-focus object plane position in standby in response to the number of reset times reaching or exceeding a given threshold.

6. A focus control device comprising:
a processor comprising hardware, wherein the processor is configured to:
   set a plurality of regions, each including a plurality of pixels, in an image acquired by an image sensor;
   calculate an autofocus (AF) evaluation value of each of the plurality of regions set;
   set a region, in the plurality of regions, determined to include a subject other than a target subject to be an invalid region;
   determine whether or not the target subject is in a low contrast state based on the AF evaluation value of a region, in the plurality of regions, other than the invalid region;
   control an in-focus object plane position based on the AF evaluation value,
   wherein the processor is configured to:
      perform a first control of the in-focus object plane position in response to determining that the target subject in the plurality of regions, other than the invalid region, is not in the low contrast state; and
      perform a second control, different from the first control, of the in-focus object plane position in response to determining that the target subject in the plurality of regions, other than the invalid region, is in the low contrast state, and
   wherein the processor is configured to:
      determine whether a variation of the AF evaluation value in the region, in the plurality of regions, other than the invalid region is smaller than a given threshold; and
      determine that the target subject is in the low contrast state in response to determining that the variation of the AF evaluation value of the region, in the plurality of regions, other than the invalid region is small than the given threshold, wherein the processor is configured to:
obtain a direction determination result for each region in some or all of the plurality of regions, by determining whether a target focusing position that is a target of the in-focus object plane position is on a near side or a far side relative to a reference position;
determine an in-focus direction based on the direction determination result:
control the in-focus object plane position based on the in-focus direction; and
determine that the target subject is in the low contrast state when the variation of the AF evaluation value as a result of moving the in-focus object plane position is smaller than the given threshold, and
wherein the processor is configured to:
set an invalid frame based on at least one of the direction determination result for each of the plurality of regions and a feature amount of the plurality of pixels in the regions; and
not move the in-focus object plane position based on the direction determination result in a frame determined to be the invalid frame.

7. The focus control device according to claim 6, wherein the processor is configured to set the invalid frame based on at least one of information on a spatial variation of the direction determination result, information on a temporal variation of the direction determination result, and information on a variation of a motion vector serving as the feature amount.

8. A focus control device comprising:
a processor comprising hardware, wherein the processor is configured to:
set a plurality of regions, each including a plurality of pixels, in an image acquired by an image sensor;
calculate an autofocus (AF) evaluation value of each of the plurality of regions set;
set a region, in the plurality of regions, determined to include a subject other than a target subject to be an invalid region;
determine whether or not the target subject is in a low contrast state based on the AF evaluation value of a region, in the plurality of regions, other than the invalid region;
control an in-focus object plane position based on the AF evaluation value,
wherein the processor is configured to:
perform a first control of the in-focus object plane position in response to determining that the target subject in the plurality of regions, other than the invalid region, is not in the low contrast state; and
perform a second control, different from the first control, of the in-focus object plane position in response to determining that the target subject in the plurality of regions, other than the invalid region, is in the low contrast state, and
wherein the processor is configured to:
determine whether a variation of the AF evaluation value in the region, in the plurality of regions, other than the invalid region is smaller than a given threshold; and
determine that the target subject is in the low contrast state in response to determining that the variation of the AF evaluation value of the region, in the plurality of regions, other than the invalid region is small than the given threshold, wherein the processor is configured to:
obtain a direction determination result for each region in some or all of the plurality of regions, by determining whether a target focusing position that is a target of the in-focus object plane position is on a near side or a far side relative to a reference position;
determine an in-focus direction based on the direction determination result;
control the in-focus object plane position based on the in-focus direction; and
determine that the target subject is in the low contrast state when the variation of the AF evaluation value as a result of moving the in-focus object plane position is smaller than the given threshold, and
wherein the processor is configured to:
determine whether a count indicating how many times switching of the movement of the in-focus object plane position from the near to the far or from the far to the near has occurred exceeds a given switching threshold; and
stop a focusing operation in response to determining that the count exceeds the given switching threshold.

9. The focus control device according to claim 8, wherein the processor is configured to reset the count indicating how many times the switching has occurred in response to a variation of the in-focus object plane position corresponding to switching from the near to the far or a variation of the in-focus object plane position corresponding to switching from the far to the near exceeding a given variation threshold.

10. A focus control device comprising:
a processor including hardware, wherein the processor is configured to:
set a plurality of regions, each including a plurality of pixels, in an image acquired by an image sensor;
calculate an autofocus (AF) evaluation value of each of the plurality of regions set;
set a region, in the plurality of regions, determined to include a subject other than a target subject to be an invalid region;
determine whether or not the target subject is in a low contrast state based on the AF evaluation value of a region, in the plurality of regions, other than the invalid region;
control an in-focus object plane position based on the AF evaluation value,
wherein the processor is configured to:
perform a first control of the in-focus object plane position in response to determining that the target subject in the plurality of regions, other than the invalid region, is not in the low contrast state; and
perform a second control, different from the first control, of the in-focus object plane position in response to determining that the target subject in the plurality of regions, other than the invalid region, is in the low contrast state, and
wherein, in performing the second control, the processor is configured to perform control to maintain a wobbling center position of a focus lens.

11. An endoscope apparatus comprising the focus control device according to claim 1.

12. A method comprising:
setting a plurality of regions, each including a plurality of pixels, in an image acquired by an image sensor;
calculating an AutoFocus (AF) evaluation value of each of the plurality of regions set;

setting a region, in the plurality of regions, determined to include a subject other than a target subject to be an invalid region;

determining whether or not the target subject is in a low contrast state based on the AF evaluation value of a region, in the plurality of regions, other than the invalid region; and controlling an in-focus object plane position based on the AF evaluation value by:
performing a first control of the in-focus object plane position in response to determining that the target subject in the plurality of regions, other than the invalid region, is not in the low contrast state; and
performing a second control, different from the first control, of the in-focus object plane position in response to determining that the target subject in the plurality of regions, other than the invalid region, is in the low contrast state,
wherein performing the second control comprises performing a reset operation of moving a focus lens to a given position and controlling the in-focus object plane position after the reset operation is performed.

13. A method comprising:
setting a plurality of regions, each including a plurality of pixels, in an image acquired by an image sensor;
calculating an autofocus (AF) evaluation value of each of the plurality of regions set;
set a region, in the plurality of regions, determined to include a subject other than a target subject to be an invalid region;
determining whether or not the target subject is in a low contrast state based on the AF evaluation value of a region, in the plurality of regions, other than the invalid region; and
controlling an in-focus object plane position based on the AF evaluation value, by:
performing a first control of the in-focus object plane position in response to determining that the target subject in the plurality of regions, other than the invalid region, is not in the low contrast state; and
performing a second control, different from the first control, of the in-focus object plane position in response to determining that the target subject in the plurality of regions, other than the invalid region, is in the low contrast state, and
wherein the method further comprises:
determining whether a variation of the AF evaluation value in the region, in the plurality of regions, other than the invalid region is smaller than a given threshold; and
determining that the target subject is in the low contrast state in response to determining that the variation of the AF evaluation value of the region, in the plurality of regions, other than the invalid region is small than the given threshold,
wherein the method further comprises:
obtaining a direction determination result for each region in some or all of the plurality of regions, by determining whether a target focusing position that is a target of the in-focus object plane position is on a near side or a far side relative to a reference position;
determining an in-focus direction based on the direction determination result;
controlling the in-focus object plane position based on the in-focus direction; and
determining that the target subject is in the low contrast state when the variation of the AF evaluation value as a result of moving the in-focus object plane position is smaller than the given threshold, and wherein the method further comprises:
setting an invalid frame based on at least one of the direction determination result for each of the plurality of regions and a feature amount of the plurality of pixels in the regions; and
not moving the in-focus object plane position based on the direction determination result in a frame determined to be the invalid frame.

14. A method comprising:
setting a plurality of regions, each including a plurality of pixels, in an image acquired by an image sensor;
calculating an autofocus (AF) evaluation value of each of the plurality of regions set;
set a region, in the plurality of regions, determined to include a subject other than a target subject to be an invalid region;
determining whether or not the target subject is in a low contrast state based on the AF evaluation value of a region, in the plurality of regions, other than the invalid region; and
controlling an in-focus object plane position based on the AF evaluation value, by:
performing a first control of the in-focus object plane position in response to determining that the target subject in the plurality of regions, other than the invalid region, is not in the low contrast state; and
performing a second control, different from the first control, of the in-focus object plane position in response to determining that the target subject in the plurality of regions, other than the invalid region, is in the low contrast state, and
wherein the method further comprises:
determining whether a variation of the AF evaluation value in the region, in the plurality of regions, other than the invalid region is smaller than a given threshold; and
determining that the target subject is in the low contrast state in response to determining that the variation of the AF evaluation value of the region, in the plurality of regions, other than the invalid region is small than the given threshold,
wherein the method further comprises:
obtaining a direction determination result for each region in some or all of the plurality of regions, by determining whether a target focusing position that is a target of the in-focus object plane position is on a near side or a far side relative to a reference position;
determining an in-focus direction based on the direction determination result;
controlling the in-focus object plane position based on the in-focus direction; and
determining that the target subject is in the low contrast state when the variation of the AF evaluation value as a result of moving the in-focus object plane position is smaller than the given threshold, and
wherein the method further comprises:
determining whether a count indicating how many times switching of the movement of the in-focus object plane position from the near to the far or from the far to the near has occurred exceeds a given switching threshold; and
stop a focusing operation in response to determining that the count exceeds the given switching threshold.

15. A method comprising:
setting a plurality of regions, each including a plurality of pixels, in an image acquired by an image sensor;
calculating an autofocus (AF) evaluation value of each of the plurality of regions set;
setting a region, in the plurality of regions, determined to include a subject other than a target subject to be an invalid region;
determining whether or not the target subject is in a low contrast state based on the AF evaluation value of a region, in the plurality of regions, other than the invalid region; and
controlling an in-focus object plane position based on the AF evaluation value by:
  performing a first control of the in-focus object plane position in response to determining that the target subject in the plurality of regions, other than the invalid region, is not in the low contrast state; and
  performing a second control, different from the first control, of the in-focus object plane position in response to determining that the target subject in the plurality of regions, other than the invalid region, is in the low contrast state,
  wherein performing the second control comprises performing control to maintain a wobbling center position of a focus lens.

* * * * *